(12) United States Patent
Thaveeprungsriporn et al.

(10) Patent No.: US 8,761,853 B2
(45) Date of Patent: Jun. 24, 2014

(54) DEVICES AND METHODS FOR NON-INVASIVE OPTICAL PHYSIOLOGICAL MEASUREMENTS

(75) Inventors: Visit Thaveeprungsriporn, Bangkok (TH); Md Irwan Bin Md Kassim, Singapore (SG); Nyan Myo Naing, Singapore (SG); Mohamad Sulhede Bin Samsudin, Singapore (SG)

(73) Assignee: Nitto Denko Corporation, Osaka (JP)

( * ) Notice: Subject to any disclaimer, the term of this patent is extended or adjusted under 35 U.S.C. 154(b) by 721 days.

(21) Appl. No.: 13/010,705

(22) Filed: Jan. 20, 2011

(65) Prior Publication Data
US 2012/0190944 A1 Jul. 26, 2012

(51) Int. Cl.
*A61B 5/1455* (2006.01)

(52) U.S. Cl.
USPC .............................. 600/323; 600/322; 600/335

(58) Field of Classification Search
USPC ................... 600/310, 322, 323, 324, 335, 344
See application file for complete search history.

(56) References Cited

U.S. PATENT DOCUMENTS

| | | | |
|---|---|---|---|
| 5,140,990 A | 8/1992 | Jones et al. | |
| 6,400,972 B1 | 6/2002 | Fine | |
| 7,239,905 B2 | 7/2007 | Kiani-Azarbayjany et al. | |
| 7,313,425 B2 | 12/2007 | Finarov et al. | |
| 7,389,131 B2 * | 6/2008 | Kanayama | 600/322 |
| 7,672,702 B2 * | 3/2010 | Hwang et al. | 600/316 |
| 2010/0056880 A1 * | 3/2010 | Cho et al. | 600/323 |
| 2010/0298678 A1 * | 11/2010 | Klomhaus | 600/344 |

FOREIGN PATENT DOCUMENTS

WO     WO 03028549 A2      4/2003

OTHER PUBLICATIONS

John Allen, Photoplethysmography and its application in clinical physiological measurement, Physiological Measurement, Feb. 20, 2007, pp. R1-R39, vol. 28, IOP Publishing Ltd, United Kingdom.
W. Karlen et al., Capillary Refill Time Assessment Using a Mobile Phone Application (iRefill), American Society of Anethesiologists Annual Meeting, Oct. 17, 2010, pp. 1-2, American Society of Anesthesiologists, San Diego, United States.

* cited by examiner

*Primary Examiner* — Eric Winakur
(74) *Attorney, Agent, or Firm* — Sughrue Mion, PLLC

(57) ABSTRACT

An optical measurement device and method of use provides non-invasive physiological measurements from a predetermined location on a body part of a user. The optical measurement device provides an illumination and detection assembly configured to generate and detect light of a predetermined wavelength range in the form of a photoplethysmography (PPG) signal, as well as a pressure detection assembly configured to detect an amount of pressure applied to the measurement device by the user being measured. A feedback unit, such as a portable display device, provides the user real-time feedback of the detected PPG signal and level of applied pressure so that the user may adjust the amount of applied pressure to improve the quality of the detected PPG signal.

38 Claims, 22 Drawing Sheets

DEVICES AND METHODS FOR NON-INVASIVE OPTICAL PHYSIOLOGICAL MEASUREMENTS

BACKGROUND

1. Field of the Invention

This invention relates to devices and methods for non-invasive optical physiological measurements, including the detection of a photoplethysmography (PPG) signal from a user, and more particularly to a pressure detection assembly of an optical measurement device which detects an amount of pressure applied by the user to the device, and a feedback unit which aids the user in determining an optimal PPG signal.

2. Description of the Related Art

Optical monitoring of physiological characteristics utilizes the detection of light transmitted through a location of a user being measured. Photoplethysmography (PPG) is an optical measurement technique used to detect blood volume changes in the microvascular bed of living tissue, typically by detecting light transmitted through the ear lobe or fingertip. As arterial pulsations enter the capillary bed, changes in the volume of the blood vessels or characteristics of the blood itself modify the optical properties of the capillary bed. The PPG signal is used to measure saturation of peripheral oxygen (SpO2), which is an estimation of the level of oxygen saturation in a fluid, such as blood. The PPG signal can also be used to measure blood pressure.

A device such as a pulse oximeter is an accepted standard in clinical practice, and provides for measuring enhanced optical pulsatile signals emitted by the changes in the volume of blood flowing through a user. The pulse oximeter generally has a pair of small light emitting diodes (LEDs) facing a photodiode, with a translucent part of the user's body, usually a fingertip or an earlobe, positioned there between. The light from the LEDs passes through the tissue and is detected by the photodiode. One LED is red, with wavelength of approximately 660 nanometers (nm), and the other is infrared, with a wavelength of approximately 905, 910 or 940 nm. Absorption at these wavelengths differs significantly between oxyhemoglobin and its deoxygenated form. Therefore, the ratio of oxyhemoglobin to deoxyhemoglobin can be calculated from the ratio of the absorption of the red and infrared light, i.e. the ratio of red light to infrared light absorption of pulsating components at the measuring site.

The basic form of PPG technology requires only a few optoelectronic components: a light source to illuminate the tissue (e.g. skin) and a photodetector to measure the small variations in light intensity associated with changes in perfusion in a catchment volume. FIG. 1 illustrates a graphical representation of a PPG signal 100, which can generally be divided into two components: an AC component 102 due to the absorption of light in pulsatile arterial blood volume 106; and a DC component 104 caused by the absorption produced by non-pulsatile arterial blood—i.e. venous blood and capillary blood 108, and tissue absorption 110.

In FIG. 1, this AC component 102 is superimposed onto a large quasi-DC component 104 that relates to the tissues and to the average blood volume. This DC component 104 varies slowly due to respiration, vasomotor activity and vasoconstrictor waves. With suitable electronic filtering and amplification, both the AC component 102 and DC component 104 can be extracted for subsequent pulse wave analysis.

Two important characteristics of the PPG AC pulse waveform 102 have been described and are illustrated in FIG. 2, where the appearance of the pulse waveform was defined as two phases: a first anacrotic phase 112 being the rising edge of the pulse, and a second catacrotic phase 114 being the falling edge of the pulse. The first phase 112 is primarily concerned with systole, while the second phase 114 represents diastole and wave reflections 116 from the periphery. A dicrotic notch 118 is usually seen in the second catacrotic phase 114 of subjects with healthy compliant arteries.

The majority of PPG devices currently available rely on simple thresholding, or peak detection algorithms, to find the principal peaks in a detected signal. However, these methods are unreliable when the detected signal is less than ideal. Particular problems may be encountered when the baseline of the AC signal component becomes noisy or complex, as can occur even with mild movement artifacts.

SUMMARY

Described herein is an optical measurement device for obtaining non-invasive physiological measurements from a portion of living tissue and method of using the same, which more particularly includes a pressure detection assembly configured to detect and display an amount of pressure applied by a body part of a user to the device during the optical measurement. When a user applies an appropriate amount of pressure to the optical measurement device, the resulting signal-to-noise ratio of the detected optical measurement signal, such as a photoplethysmography signal, can be increased, and a more accurate measurement can be obtained from the user. An optimum pressure can be determined in real-time by analyzing the detected optical measurement signal and correlating a high signal-to-noise ratio portion of the signal with a corresponding applied pressure. The user is then provided real-time feedback indicating whether the amount of pressure being applied by the user should be increased, decreased or maintained at the same level in order to continually obtain the highest quality signal. The optical measurement device can therefore provide an optimal pressure determination customized for each individual user, thereby obtaining a resulting optimal measurement signal for each user.

In one aspect of the invention, there is provided an optical measurement device comprising an illumination and detection assembly configured to output light to a portion of living tissue of a user and detect transmitted or reflected light as a signal; a pressure assembly configured to detect an amount of pressure applied to the illumination and detection assembly by the portion of living tissue of the user; and a feedback unit configured to correlate the quality of the detected signal with the amount of applied pressure and provide feedback related to the correlation to the user.

The feedback may be an indication of whether the user should adjust the amount of pressure being applied to the illumination and detection assembly.

The feedback may display a range of optimal applied pressures along with the actual applied pressure being applied by the user.

The range of optimal applied pressures may correspond to a state of zero transmural pressure.

The feedback may be a request to the user to increase, decrease or maintain the applied pressure.

The feedback may be a real-time visual output of the detected signal and detected applied pressure.

The feedback unit may be a portable computer including a processor, memory and a display.

The illumination and detection assembly, pressure assembly and feedback unit may be integrated into a portable device.

The portable device may be configured with a plurality of illumination and detection assemblies and a plurality of pressure assemblies.

The illumination and detection assembly and the pressure assembly may communicate with the feedback unit over a wireless network.

The detected signal may be a photoplethysmography (PPG) signal.

In another aspect of the invention, a method for detecting a physiological signal using an optical measurement device comprises: illuminating a portion of living tissue of a user and detecting transmitted or reflected light as a signal using an illumination and detection assembly; detecting an amount of pressure applied by the portion of living tissue of the user to the illumination and detection assembly using a pressure detection assembly; correlating the quality of the detected signal with the amount of applied pressure; and providing feedback related to the correlation to the user using a feedback unit.

The method may include providing an indication to the user of whether the amount of pressure being applied to the illumination and detection assembly should be adjusted.

The method may include displaying a range of optimal applied pressures along with the actual applied pressure being applied by the user.

The method may include providing a range of optimal applied pressures along which corresponds to a state of zero transmural pressure.

The method may include requesting the user to increase, decrease or maintain the applied pressure.

The method may include displaying a real-time visual output of the detected signal and the detected applied pressure.

The method may include providing feedback on a display of a computer with a processor and a memory.

The illumination and detection assembly, pressure assembly and feedback unit may be integrated into a portable device.

The portable device may be configured with a plurality of illumination and detection assemblies and a plurality of pressure assemblies.

The method may include wirelessly communicating between the feedback unit and the illumination and detection assembly and pressure assembly.

The detected signal may be a photoplethysmography (PPG) signal.

In another aspect of the invention, a computer program product is provided for detecting a physiological signal using an optical measurement device, the computer program product embodied on a computer readable medium and when executed by a computer with a processor and a memory, performs the method comprising: illuminating a portion of living tissue of a user and detecting transmitted or reflected light as a signal using an illumination and detection assembly; detecting an amount of pressure applied by the portion of living tissue of the user to the illumination and detection assembly; correlating the quality of the detected signal with the amount of applied pressure; and providing feedback related to the correlation to the user.

Additional aspects related to the invention will be set forth in part in the description which follows, and in part will be apparent from the description, or may be learned by practice of the invention. Aspects of the invention may be realized and attained by means of the elements and combinations of various elements and aspects particularly pointed out in the following detailed description and the appended claims.

It is to be understood that both the foregoing and the following descriptions are exemplary and explanatory only and are not intended to limit the claimed invention or application thereof in any manner whatsoever.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. Specifically.

DETAILED DESCRIPTION

An optical measurement device for obtaining non-invasive physiological measurements and method of using the same is described more fully herein, including the pressure detection assembly configured to detect and display an amount of pressure applied by a body part of a user to the device during the optical measurement. When the user applies an appropriate amount of pressure to the optical measurement device, the resulting signal-to-noise ratio of the detected optical measurement signal can be increased, and a more accurate measurement signal can be obtained from the user. An optimal pressure can be determined in real-time by analyzing the detected optical measurement signal and correlating a high signal-to-noise ratio portion of the signal with a corresponding applied pressure. The user is then provided real-time feedback indicating whether the amount of pressure being applied by the user should be increased, decreased or maintained at the same level. The optical measurement device can therefore provide an optimum pressure determination customized for each individual user, thereby obtaining a resulting optimum measurement signal for each user.

In the following detailed description, reference will be made to the accompanying drawings. The aforementioned accompanying drawings show by way of illustration and not by way of limitation, specific embodiments and implementations consistent with principles of the present invention. These implementations are described in sufficient detail to enable those skilled in the art to practice the invention, and it is to be understood that other implementations may be utilized and that structural changes and/or substitutions of various elements may be made without departing from the scope and spirit of present invention. The following detailed description is, therefore, not to be construed in a limited sense. Additionally, the various embodiments of the invention as described may be implemented in the form of software running on a general purpose computer, in the form of a specialized hardware, or combination of software and hardware.

The acquisition of a physiological signal representing a change in the volume of an organ in the body through the use of optical measurement is known as a photoplethysmograph (PPG). Obtaining optical PPG signals typically requires application of external pressure on the body surface which is being measured. The pressure is required in order to obtain a good quality PPG signal with a high signal to noise ratio.

Figure 3:
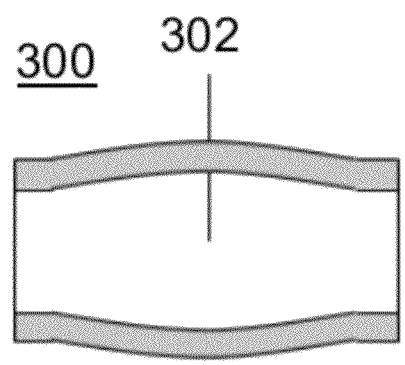
FIG. 3 is an illustration of a cross-section of a blood vessel when a low external pressure is applied.
Figure 4:
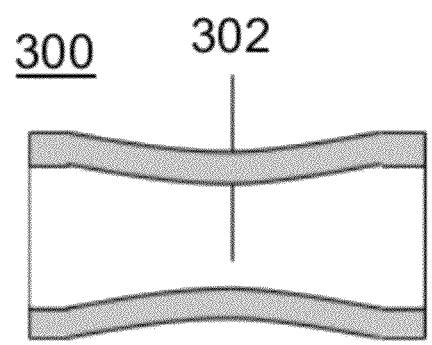
FIG. 4 is an illustration of the cross-section of the blood vessel when a high external pressure is applied.
Figure 5:
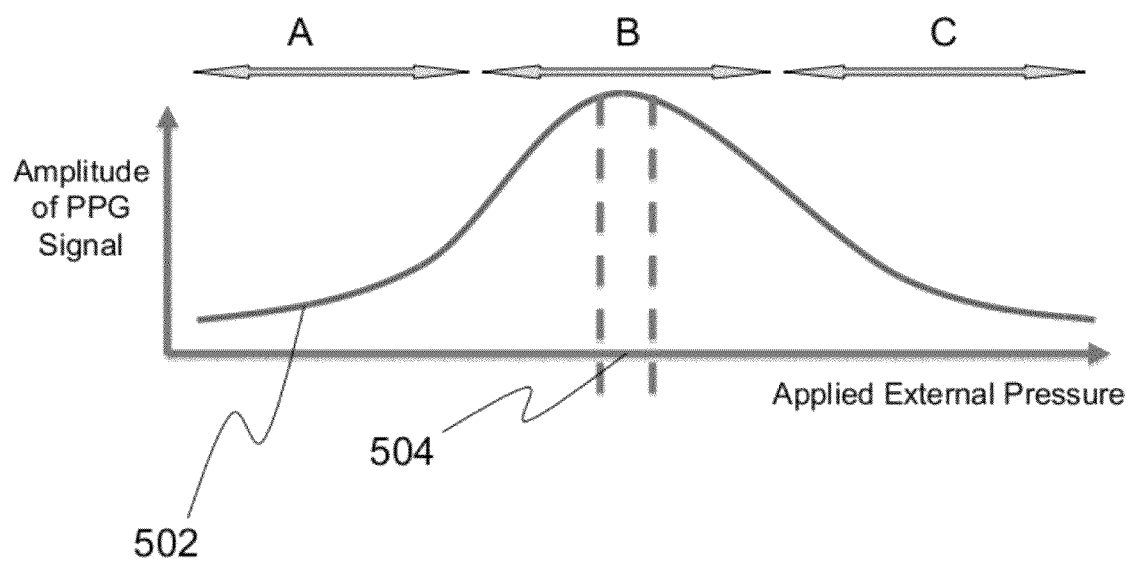
FIG. 5 is a graphical illustration of an amplitude of a PPG signal received during increasing amounts of external pressure in a state of zero transmural pressure.

However, the externally-applied pressure cannot be too large or too small, or the quality of the detected PPG signal will be low. For example, as illustrated in a cross section of a blood vessel 300 in FIG. 3, in the event of an insufficient exertion of external force as compared to internal arterial pressure at a measurement site 302, the internal pressure is too low to obtain a proper measurement, and low PPG signals are obtained. On the contrary, as illustrated in FIG. 4, the application of too much external force causes the blood vessel 300 to be occluded at the measurement site 302 where the pressure is applied, resulting in resistance of regular blood flow and generating skewed PPG signal data. If the external pressure is too small or too high, the reaction pressure at the wall of the blood vessel 300 is low, and thus a small PPG signal will be observed. FIG. 5 is a graphical illustration of the amplitude 502 of a measured PPG signal in comparison with an amount of applied external pressure. With a low applied pressure in range A, the amplitude 502 is correspondingly low. As the applied pressure is increased, in range B, the amplitude also increases. However, when the applied pressure increases beyond a certain point, the amplitude decreases again, as shown in range C.

To obtain a strong PPG signal, the external pressure should be sufficient to minimize transmural pressure such that the external pressure is equal to the internal pressure. Further illustrated in FIG. 5 is a range 504 within range B where the amplitude of the PPG signal is at its peak. Within this range 504, an externally-applied pressure is instantaneously balanced with the internal arterial pressure, thus resulting in a state of zero transmural pressure. At zero transmural pressure, the arterial walls are unloaded and the arteries will not change in size. Consequently, the blood volume within the arteries at the measured region will not change and can be accurately measured to provide a good quality PPG signal.

In an exemplary embodiment, the pressure assembly seeks to achieve and to maintain an optimal pressure for obtaining an optimum PPG signal over an extended period of time. By providing real-time, instantaneous feedback to a user being measured, the user is able to instantly adjust the amount of pressure being applied to the device in order to obtain an optimum PPG signal. However, the optimum pressure may not only be a result of a state of zero transmural pressure, but may also result from the effects of absorption and scattering paths of light as light travels in and out of a portion of tissue of a user being measured. For example, where the pressure is too low, a light source may not be able to penetrate the tissue surrounding the blood vessel which is being measured. Therefore, light may not travel in and out of the finger effectively enough for a good PPG signal to be detected. Where the pressure is too high, light may be absorbed or scattered such that the amount of light detected is insufficient to obtain a good PPG signal.

In one exemplary embodiment, the device may provide feedback to the user indicating whether the user is applying insufficient pressure, too much pressure or the correct amount of pressure. The feedback to the user may be visual or auditory in the form of a visual display or audible sounds, and may particularly be a display of the real-time PPG signal being captured by the device. The feedback may also be a more simplified display indicating whether the user should take action to increase or reduce the amount of pressure being applied to the device. In another embodiment, the feedback may be in the form of tactile feedback, wherein the device produce's e.g. a small vibration when the applied pressure is at an optimum range.

Exemplary embodiments described herein seek to provide a device and method capable of augmenting signal to noise ratio in an optical signal of an illuminated region at a measuring site of a body part of a user. Exemplary embodiments also provide for detecting the optical response formed by both light reflected from the measuring site and the light transmitted through the measuring site. Exemplary embodiments described herein utilize redirecting reflections of light on its way towards the measuring site (i.e. blood vessels) back to the region of interest.

In an additional exemplary embodiment, the device may perform a series of calibration steps for each individual user in order to determine an optimum range of pressure for each individual. The subsequent steps of capturing the PPG signal will then use the predetermined optimum range as the benchmark for obtaining an optimum PPG signal.

I. Device Overview

Figure 6A:
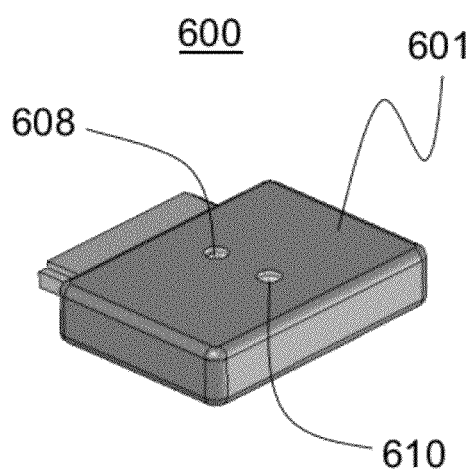
FIG. 6A is an illustration of an optical measurement device, according to an exemplary embodiment.
Figure 6B:
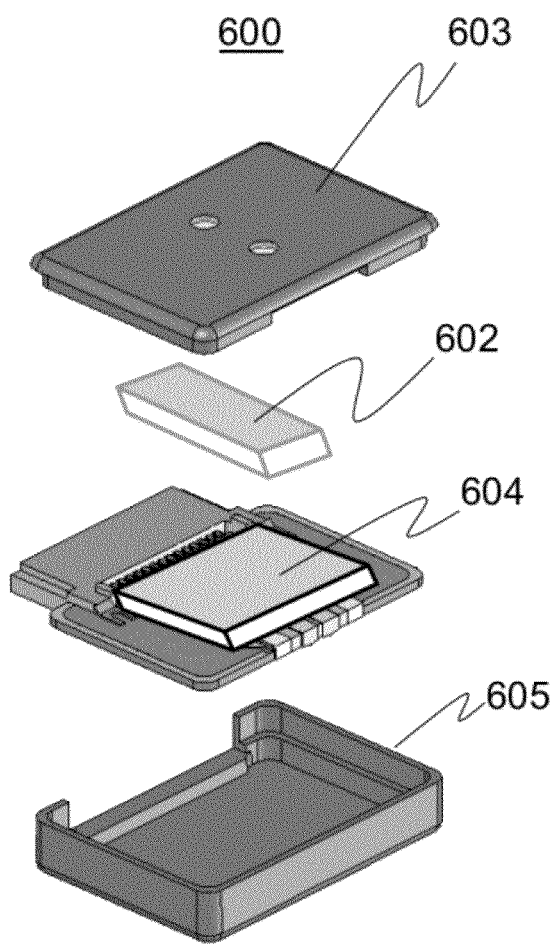
FIG. 6B is an exploded view illustration of the optical measurement device, including an illumination and detection assembly and a pressure detection assembly, according to an exemplary embodiment.

FIG. 6A illustrates one exemplary embodiment of an optical measurement device 600, and FIG. 6B illustrates an exploded view of the optical measurement device 600, showing the arrangement of an illumination and detection assembly 602 and a pressure detection assembly 604. As illustrated in FIG. 6A, the illumination and detection assembly 602 and pressure detection assembly 604 may be integrated as a single, compact optical measurement device 600 surrounded by a housing 601 for portable use. In the exploded view in FIG. 6B, the housing 601 is shown divided into a top casing 603 and a base casing 605, with the illumination and detection assembly 602 and pressure detection assembly 604 enclosed therein. The integration of the pressure detection assembly 604 with the illumination and detection assembly 602 provides a simple, comfortable interaction for the user, and the use of a pressure detection assembly 604 which provides real-time feedback to the user improves the quality, or amplitude, of the received PPG signals. The optical measurement device 600 is connected with a feedback unit 606 (see FIG. 9A), which receives the PPG signals and pressure measurements from the optical measurement device 600 and provides feedback to the user regarding the amount of pressure being applied.

The illumination and detection assembly 602 may be referred to as a PPG sensor, and includes a light source 608 and a plurality of light detectors 610 (see FIG. 17), where the light source 608 propagates light through a portion of living tissue at a measurement site of a user. The light detectors 610 then detect light which is transmitted through the portion of living tissue of the user or which is reflected from the portion of living tissue of the user.

Figure 7A:
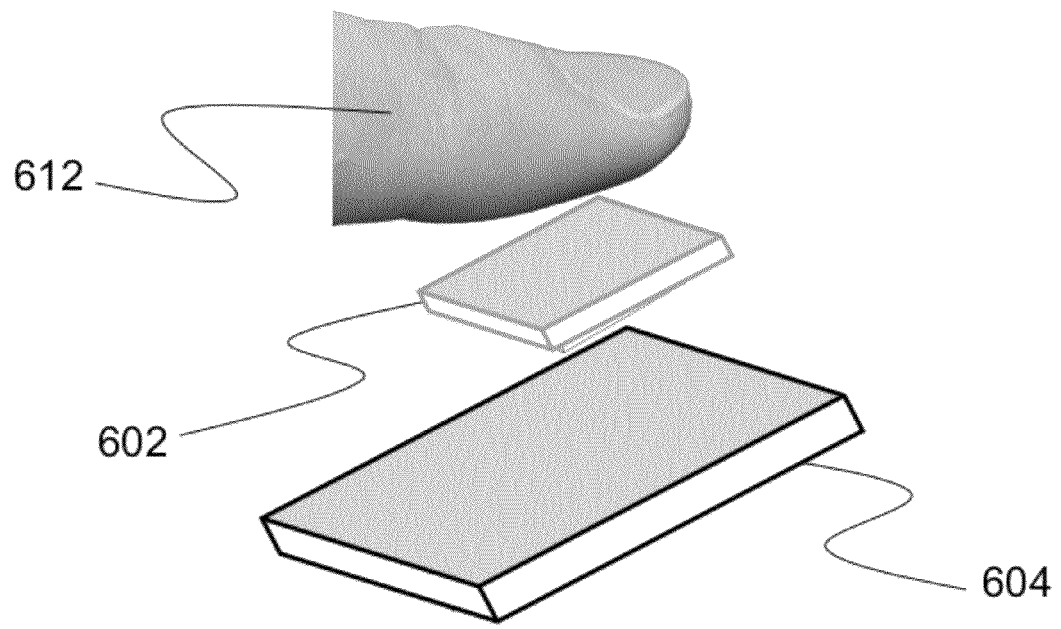
FIGS. 7A and 7B are expanded view illustrations of the illumination and detection assembly and a pressure detection assembly of the optical measurement device and a method of use with a human finger, and according to one exemplary embodiment.
Figure 7B:
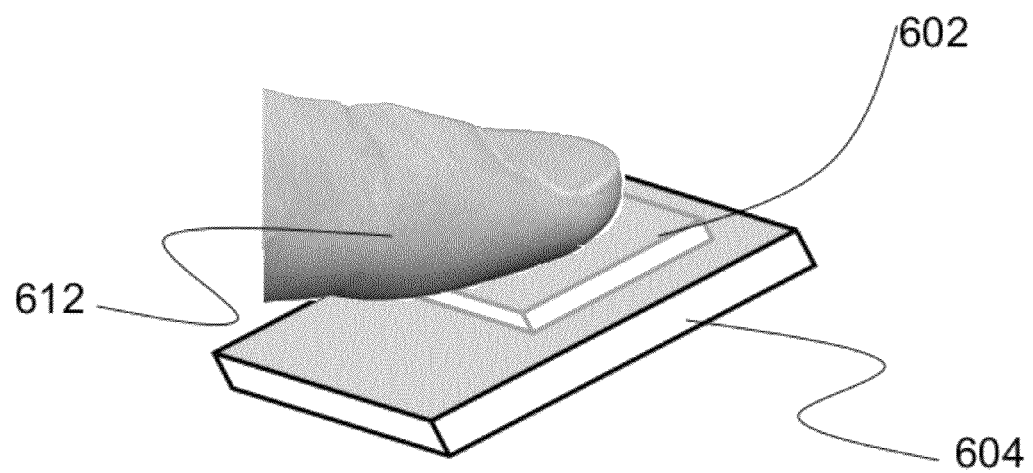

In one exemplary embodiment, the pressure detection assembly 604 is a pressure sensor that detects the amount of pressure that has been applied by a body part of the user, such as a finger. The pressure sensor may be a thin film flexible printed circuit. Nevertheless, any other force measuring device that is capable of sensing an applied contact force may be used. As illustrated in the exploded view of the optical measurement device in FIG. 7A, the pressure sensor 604 may be positioned below the PPG sensor 602, so that the force applied by a user's finger 612 is translated through the PPG sensor 602 to the pressure sensor 604. The pressure sensor 604 then gathers and tracks the external force exerted by the user's finger 612. FIG. 7B illustrates an assembled view of the pressure sensor 604 together with the PPG sensor 602 in operation, where the user's finger 606 is placed in contact with the PPG sensor 602.

The feedback unit 606 may be a computer including a processor, a memory and optionally a display, as is further described below with regard to FIG. 22. The feedback unit 606 receives a PPG signal and pressure measurements from the optical measurement device 600, and temporally correlates the PPG signal with the pressure measurements in order to determine an optimal amount of pressure that provides an optimal PPG signal, as shown in the comparison PPG signal graph 802 and applied pressure graph 804, illustrated in FIG. 8 and described in more detail below.

Figures 9A, 9B:
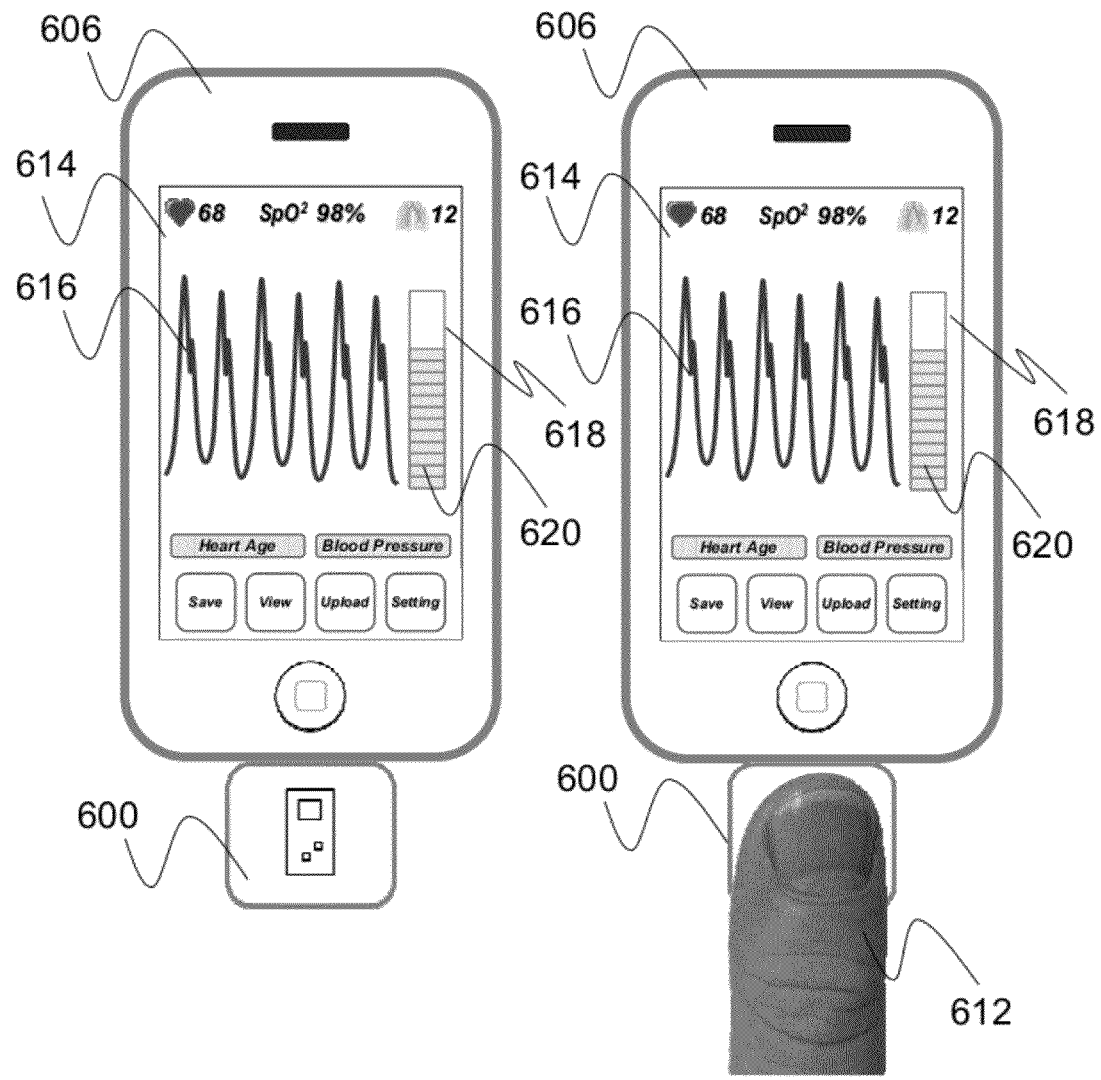
FIGS. 9A and 9B illustrate a feedback unit, such as a portable device with a display, in connection with an optical measurement device and a user's interaction therewith, according to an exemplary embodiment.

The feedback unit 606 may be provided with a display 614, as illustrated in FIGS. 9A and 9B. The display 614 may provide visual feedback to the user in the form of a graphical user interface (GUI) during the process of measuring the PPG signal. The visual feedback may be a real-time display of the detected PPG signal 616 so that the user can instantly see the effect of varying the amount of pressure being applied to the optical measurement device and adjust the amount of pressure until an optimum PPG signal is displayed. The display 614 may also provide a real-time graphical indication 618 of the pressure being applied. The graphical display 618 of the applied pressure may track the PPG signal 616 on the same graphical display (see FIG. 21A, below), or perhaps be displayed in the form of a vertical pressure status bar 620 positioned on one side of the displayed PPG signal, as illustrated in FIGS. 9A and 9B. The status bar 620 will move up and down depending on the amount of force being applied by the user. In this embodiment, the user identifies an optimal PPG signal in order to determine whether the displayed real-time PPG signal 616 can be improved. However, by displaying the detected PPG signal 616 and possibly the pressure status bar 620, the feedback unit 606 is not required to compute an amount of pressure that provides an optimum PPG signal, as the user is performing this step manually by analyzing the displayed PPG signal 616 and making adjustments without guidance by the device. FIG. 9B illustrates the feedback unit 606 and the optical measurement device 600 in operation, where a user's finger 612 is positioned on the optical measurement device 600.

Figure 10:
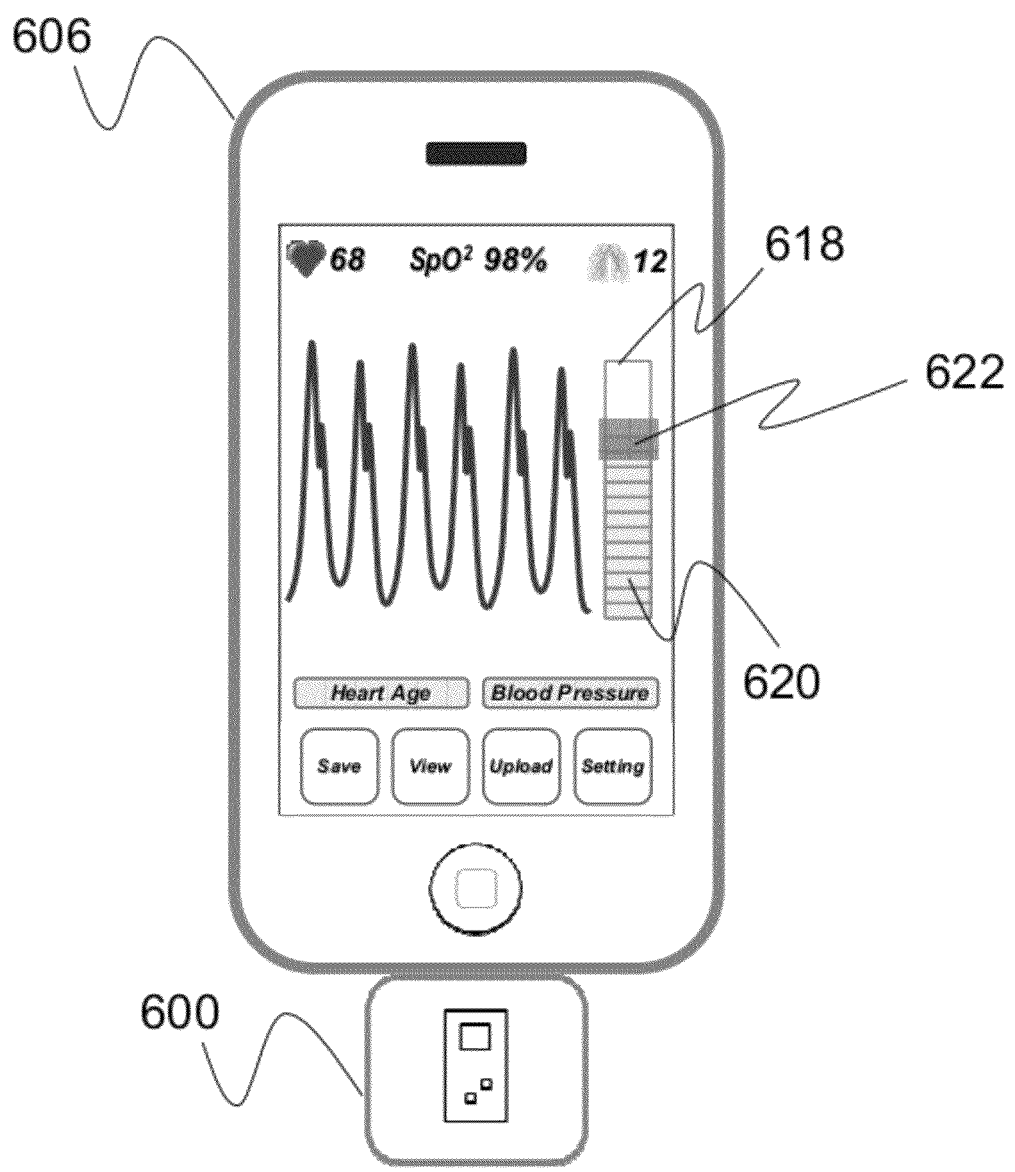
FIG. 10 illustrates a graphical user interface (GUI) on the display, including a graphical representation of a PPG signal and a graphical representation of applied pressure, according to an exemplary embodiment.

In an exemplary embodiment illustrated in FIG. 10, the feedback unit 606 may generate and display a GUI with a more simplified indication of whether the user should adjust the amount of pressure to provide more, less or the same amount. There may be any number of ways to provide this type of GUI. For example, symbols or shapes—perhaps even color-coded in a traffic-light colored display—may be displayed to tell the user to adjust the amount of force being applied. Similarly, the GUI may simply display words telling the user to "Apply More Pressure, "Apply Less Pressure," or "Apply the Same Amount of Pressure." In FIG. 10, a highlighted box 622 may be placed over the pressure status bar 620 to identify an optimum range at which pressure should be applied for a particular user. In this embodiment, the feedback unit 606 analyzes and compares the measured PPG signal and corresponding applied pressures in real-time in order to determine a range of applied pressure which provides the highest amplitude of PPG signal—usually a state of zero transmural pressure. The feedback unit 606 will then provide corresponding indicators to the user on the display 614 depending on whether the user is applying pressure within, above or below the determined range.

In an exemplary embodiment, the feedback unit 606 may not require a display, as it could provide audible commands to the user through a speaker or other audio output component. For example, the audio device could simply talk to the user to say "Apply More Pressure," "Apply Less Pressure," or "Apply the Same Amount of Pressure." The audio feedback could also be in the form of musical tones of different pitches or sounds—such as a ringing sound or buzzer sound—which are widely known as positive or negative sounds.

In another exemplary embodiment, the optical measurement device 600 may ask the user to calibrate the device before actual measurement of the PPG signal is carried out. This may involve asking the user to apply a variety of different pressures to the device during a fixed period of time, during which the feedback unit measures the PPG signal detected during that time period and determines a range of applied pressure which obtains an optimal PPG signal. For example, the user may be asked to exert pressure while following a profile of pressure ranges over a period of time, such as the force profile 808 in the applied pressure graph 804 in FIG. 8. As a result of the calibration, the device 600 is able to obtain a range of applied pressure for each individual user, rather than a generalized range which will not be accurate depending on the individual user being measured.

In one exemplary embodiment, the feedback unit 606 may be a portable device, such as a mobile phone, smartphone, personal digital assistant (PDA), tablet, netbook or laptop, although this list is not exhaustive by any means. However, the feedback unit 606 may not need to be portable, and could similarly be a computer or server. The feedback unit 606 may be connected with the optical detection device 600 in a wired or wireless fashion, or through a proprietary connector, such a universal serial bus (USB) port or the 30 pin connection used in the Apple® iPhone® (Apple Computer, Inc., Cupertino, Calif.).

Figure 11:
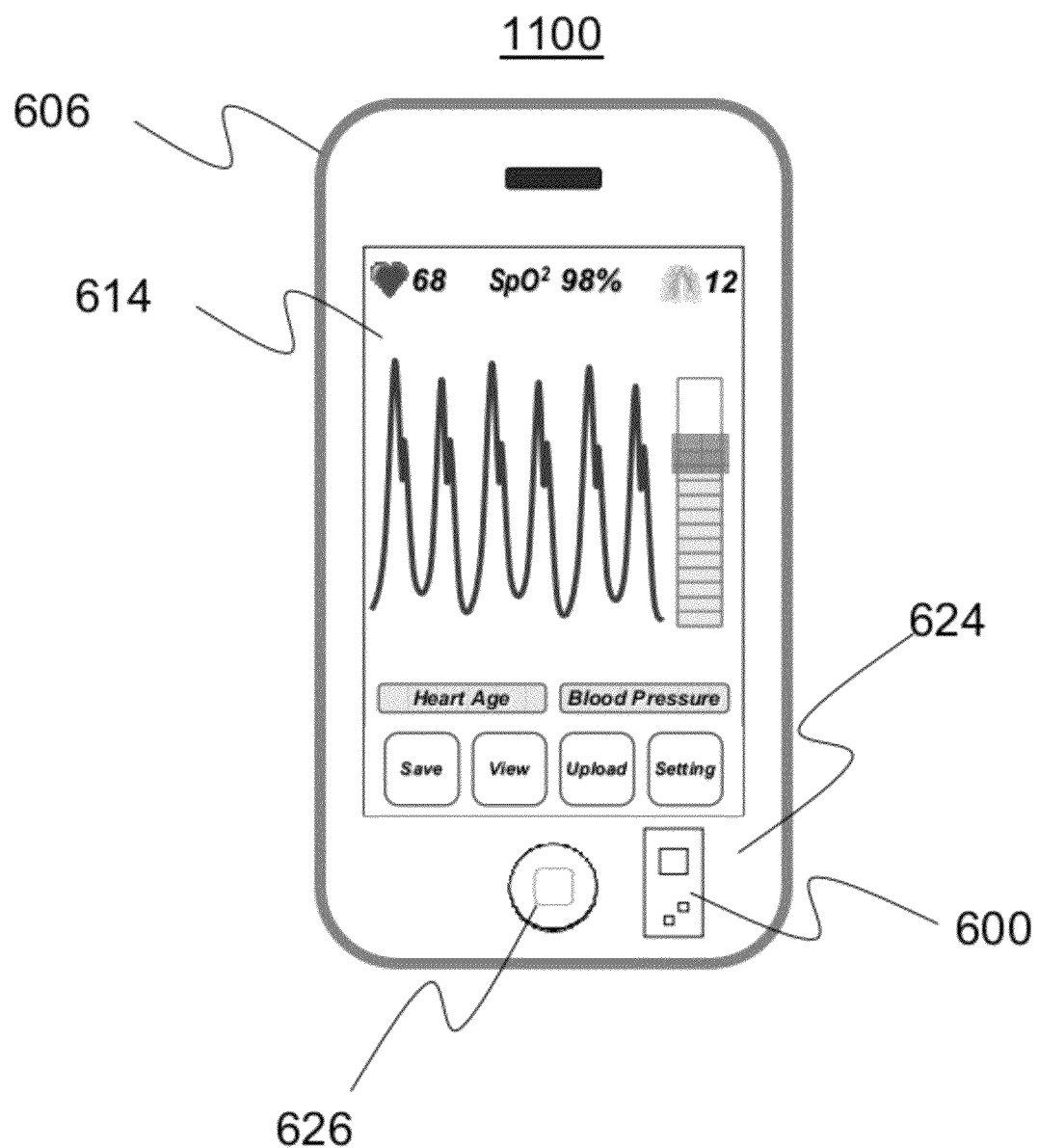
FIG. 11 illustrates a portable device integrated with an optical measurement device, according to an exemplary embodiment.
Figure 17:
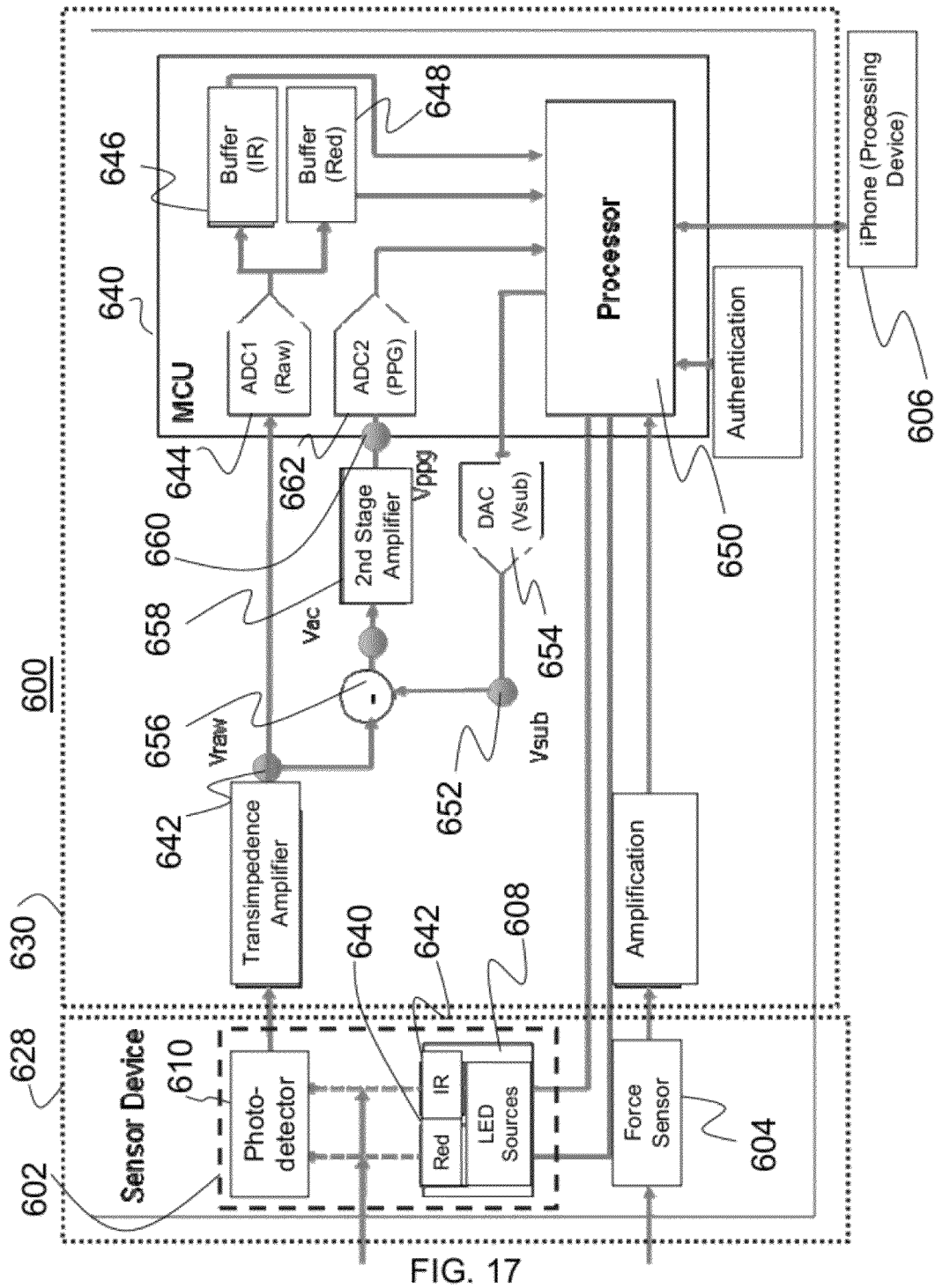
FIG. 17 is a block diagram of the optical measurement device, according to an exemplary embodiment.

In another embodiment, the portable device may be integrated with the optical detection device as a single optical measurement device 1100, as shown in FIG. 11. The optical detection device 600 is incorporated within a housing 624 of a portable device 606; in this case located near a menu button 626 of the portable device 606 and separate from a display 614. With such a configuration, the portable device 606 is capable of carrying out processing functions for the optical detection device 600, such as signal conditioning and signal processing. As described below with regard to the block diagram in FIG. 17, the optical detection device 600 integrated with the portable device 606 would only require a sensing portion 628, while a processing portion 630 would be provided by hardware and firmware of the of the portable device 606. The sensing portion 628 would include the illumination and detection assembly 602 and the pressure detection assembly 604, as illustrated in FIG. 17.

Figure 12:
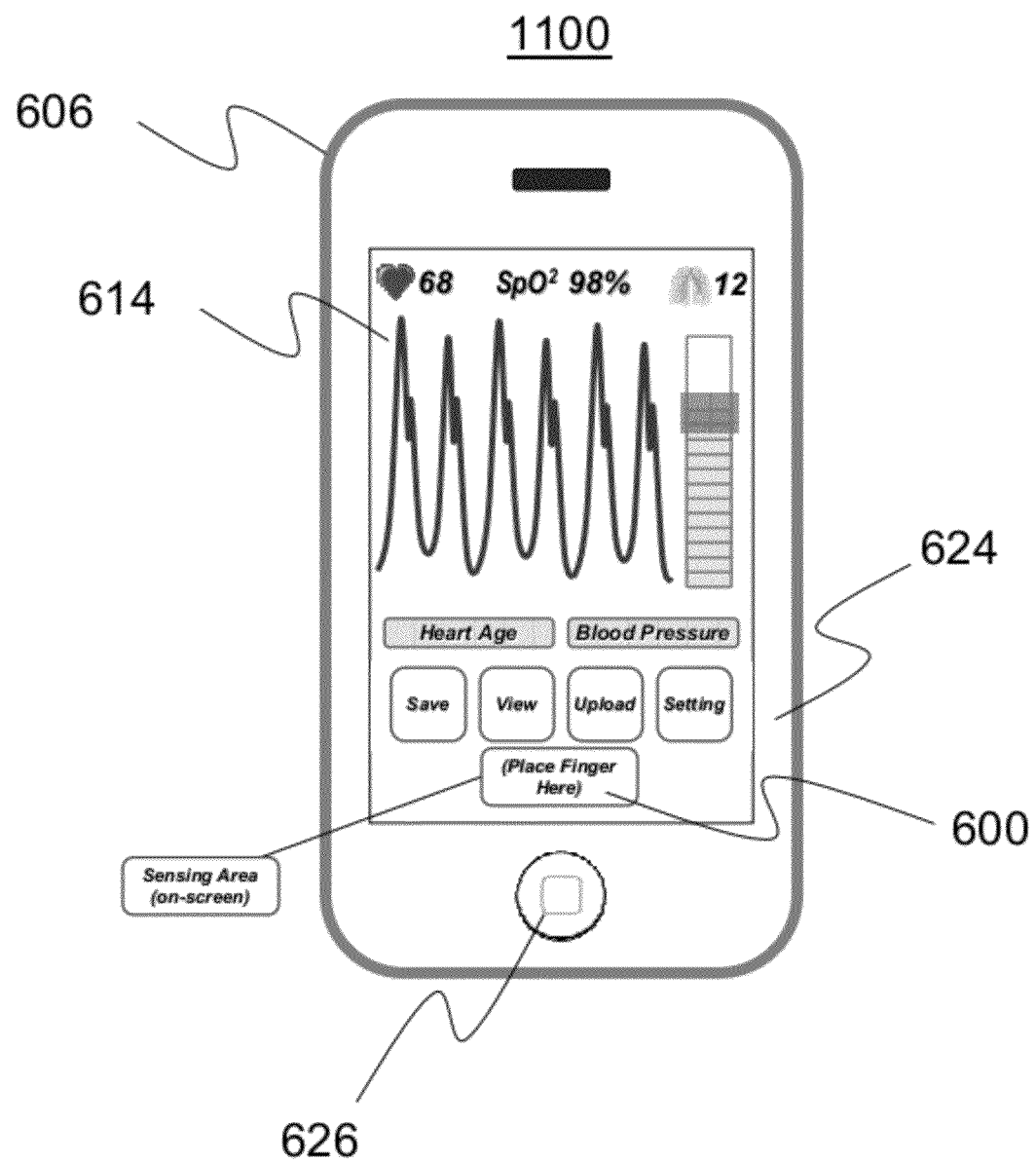
FIG. 12 illustrates an optical measurement device integrated with a touchscreen display of a portable device, according to an exemplary embodiment.

In another exemplary embodiment illustrated in FIG. 12, the optical detection device 600 may be integrated with the display 614 when the display is a touch screen display. Two openings may be created in the touch screen display to permit the transmission of light from the LED light sources and to the photodetector. The components of the touch screen display 614 would have accurate pressure-sensing capabilities to detect the amount of pressure applied on the touch screen display 614, such that the functions of the pressure detection assembly can be provided by the touch screen display 614 directly, thereby eliminating the need for a separate pressure detection assembly. Therefore, only the illumination and detection assembly of the optical detection device would be separately required, such as red and infrared (IR) LED light sources and a photodetector.

In another exemplary embodiment, the illumination and detection assembly may comprise a camera and flash of a smartphone or other portable device, such that the camera functions as the photodetector while the flash functions as the light source. The flash and camera would be located proximate to each other on the portable device, and the flash would be configured with a red LED and infrared LED to output the required wavelengths of light. In this exemplary embodiment, the pressure detection assembly would be the only significant modification required on the portable device.

Figure 13A:
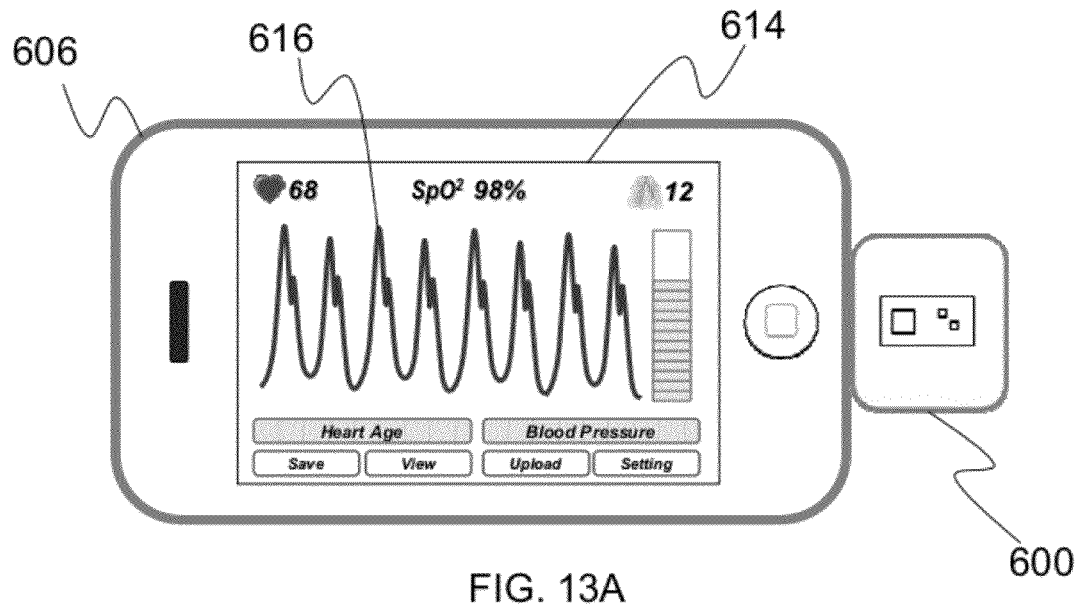
FIGS. 13A and 13B illustrate a portable device connected with an optical measurement device configured in a landscape orientation and a user's interaction therewith, according to an exemplary embodiment.
Figure 13B:
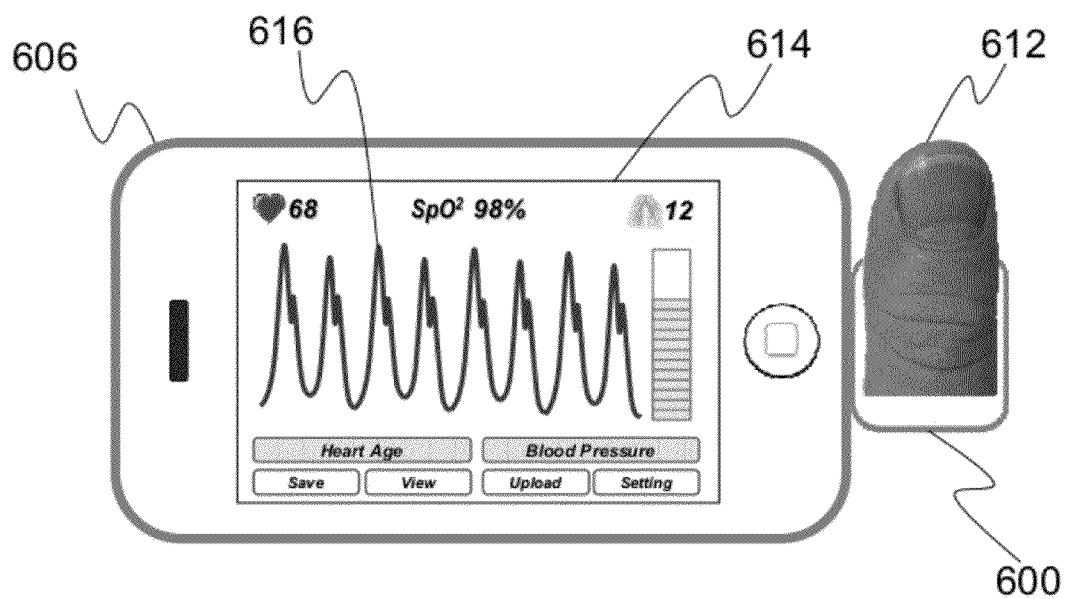

FIGS. 13A and 13B illustrate yet another exemplary embodiment, where the portable device 606 may be oriented in a landscape configuration such that the user views the display 614 horizontally and interacts with the optical detection device 600 in a way that is easier for the user to hold the portable device 606 in the user's hands. In landscape orientation, the user can place a finger 612 on the optical detection device 600 and more easily view a larger time period of the PPG signal 616.

Figure 14A:
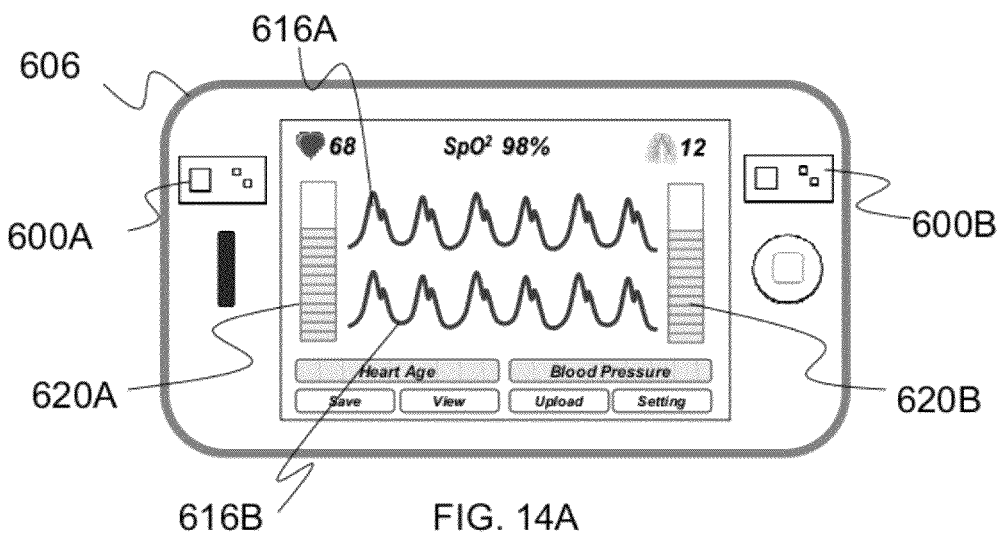
FIGS. 14A and 14B illustrate a portable device integrated with a plurality of optical measurement devices in a landscape orientation and a user's interaction therewith, according to an exemplary embodiment.
Figure 14B:
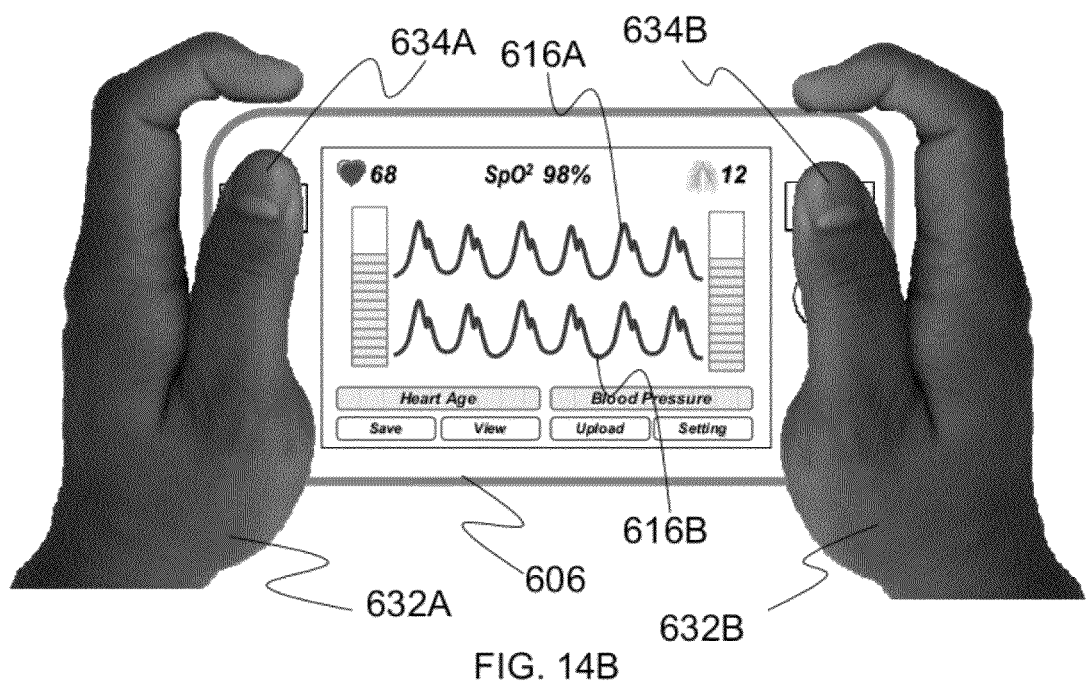
Figures 15A, 15B:
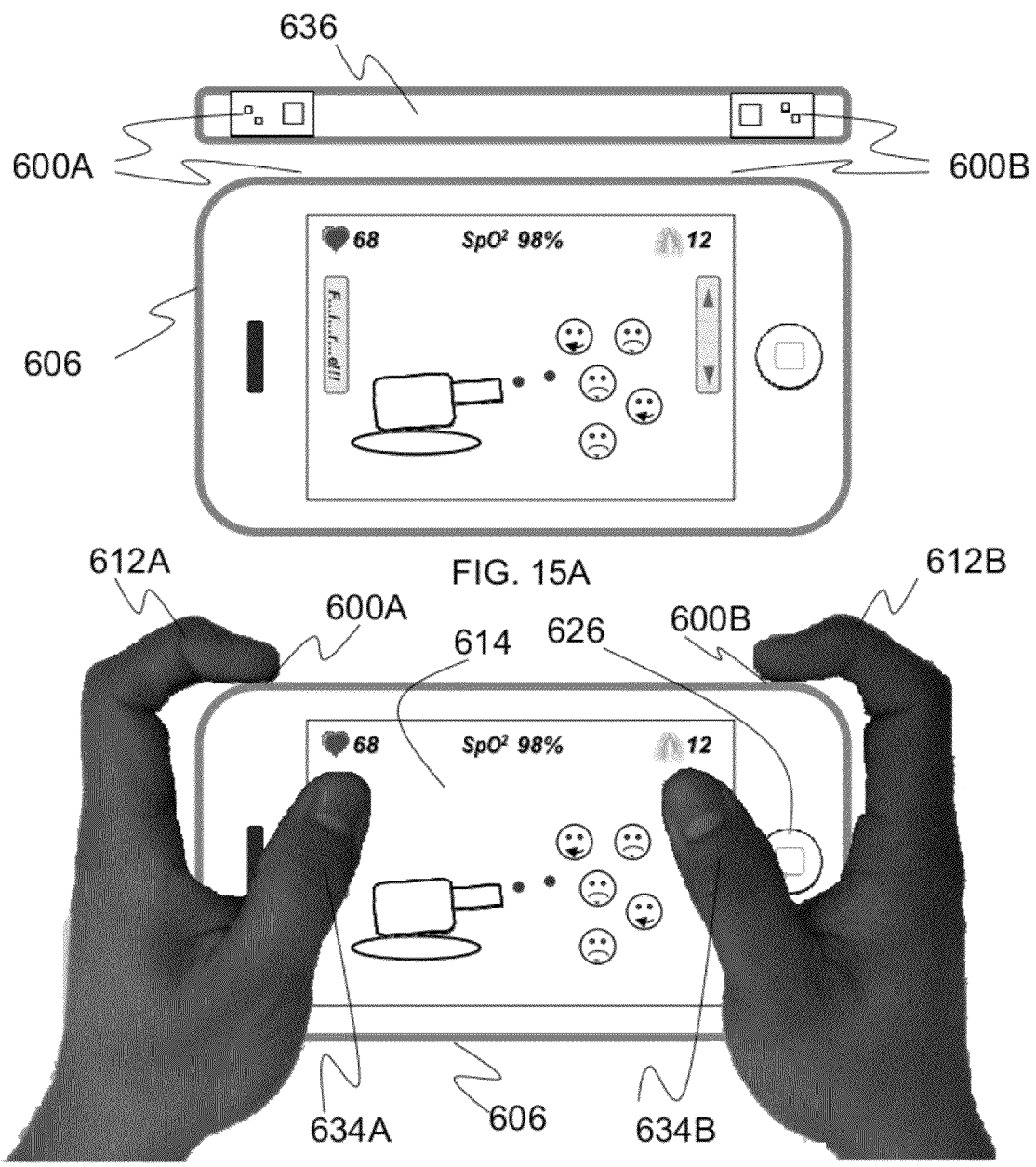
FIGS. 15A and 15B illustrate a portable device integrated with a plurality of optical measurement devices located on a side portion of the portable device, according to an exemplary embodiment.

FIGS. 14A and 14B illustrate another exemplary embodiment, where a plurality of optical detection devices 600A and 600B are integrated with the portable device 606 for interaction with the user in a landscape orientation. The use of more than one optical detection device will allow measurement of additional physiological properties, As shown in FIG. 14B, the user can easily hold the portable device 606 with both hands 632A and 632B while also placing their thumbs 634A and 634B on the corresponding optical detection devices 600A and 600B. In a similar exemplary embodiment illustrated in FIGS. 15A and 15B, the optical detection devices 600A and 600B may be located on a side portion 636 of the portable device 606, so that the user can place index fingers 612A and 612B in contact with the corresponding optical detection devices 600A and 600B in a natural configuration. In this embodiment, the user's thumbs 634A and 634B are then free to operate the portable device by interacting with the touch screen display 614 or menu button 626 while the index fingers are being sensed by the optical detection devices 600A and 600B. In the embodiments illustrated in FIGS. 14 and 15, because there are a plurality of optical detection devices 600A and 600B, there may also be a corresponding plurality of PPG signals 616A and 616B and pressure status bars 620A and 620B accordingly.

The feedback unit may also include software or other computer programmable instructions which carry out instructions relating to receiving and processing the PPG signal, the pressure measurements, and creation of the output to the user relating to the correlation of the detected PPG signal and pressure measurements.

The monitoring of (i) the PPG signal from the illumination and detection assembly and (ii) the amount of force exerted by an individual from the pressure assembly thus enables the optical measurement device to obtain an optimum PPG signal with a high signal to noise ratio. The signal to noise ratio is augmented in an optical signal. The optical measurement device provides for a PPG signal to be acquired at a zero transmural pressure that is unique to each user using the device.

The resulting optimal PPG signal provides a highly accurate measurement of various physiological parameters detected by photoplethysmography, such as a saturation level of oxygen in blood.

Figure 8:
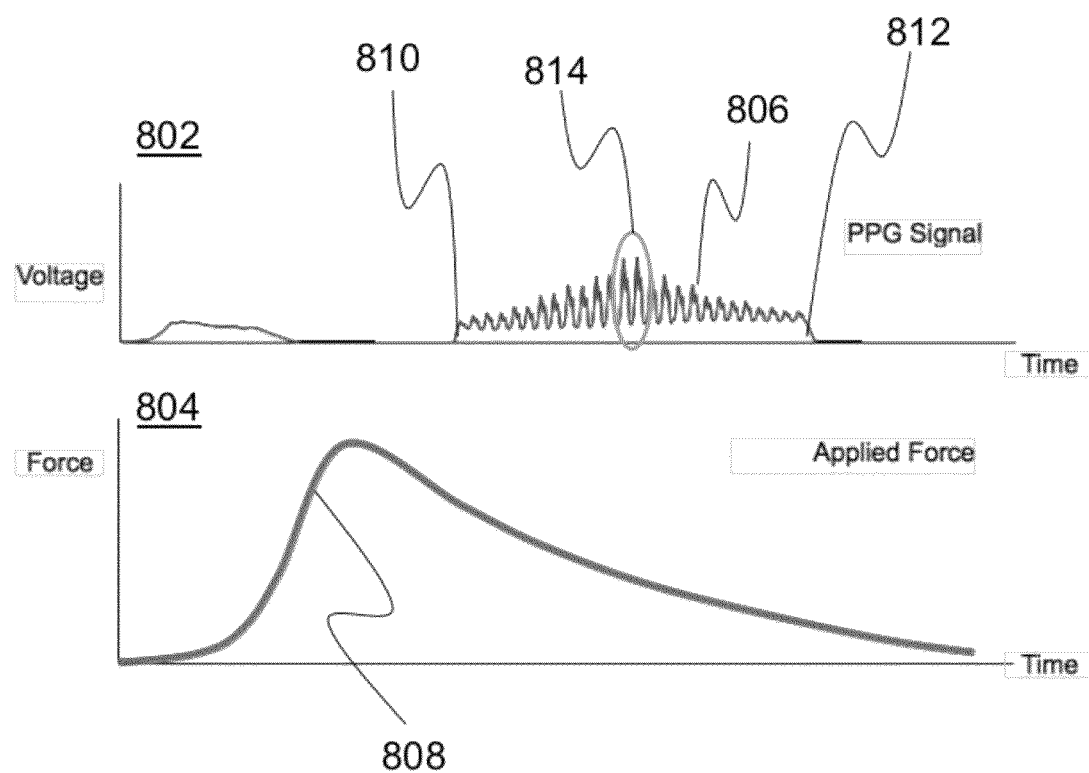
FIG. 8 illustrates a graphical comparison of a graph of measured voltage of a PPG signal over time as it corresponds to a graph of an applied amount of pressure over time.
Figure 16A:
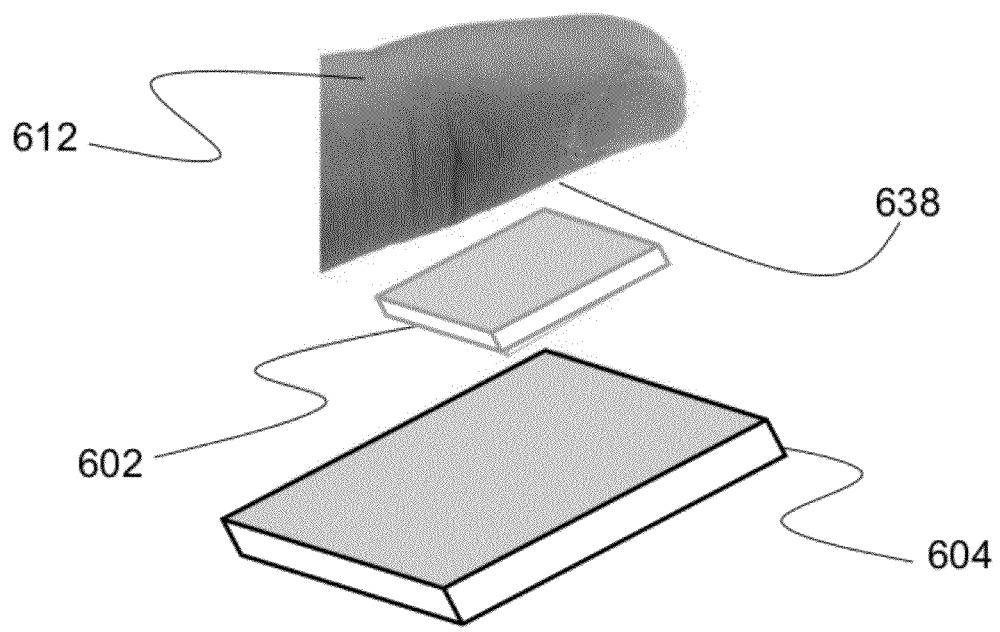
FIGS. 16A and 16B are expanded view illustrations of an alternate embodiment of a method of using the optical measurement device with the human finger to detect the blood pressure of the human, according to one exemplary embodiment.
Figure 16B:
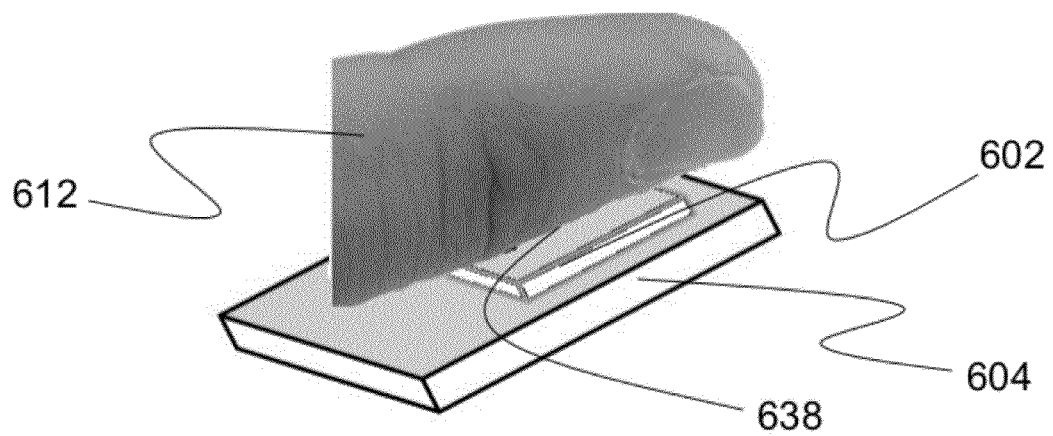

In another embodiment, the optical measurement device further includes acquisition of systolic and diastolic blood pressure parameters. One option for detecting the parameters to determine blood pressure involves placing the side 638 of the finger 612 where the digital artery lies onto the illumination and detection assembly 602, as illustrated in FIGS. 16A and 16B. As shown in FIG. 8, a PPG signal 806 in the PPG signal graph 802 is monitored while the user applies vertical downward force onto the pressure sensor 604 following a pre-determined applied force profile 808 with respect to time, as shown in the applied pressure graph 804. The basic fundamental behind this analysis is to identify when the PPG signal 806 begins to display a PPG waveform (point 810) and when the PPG signal finally dies off (point 812), as these points are indirectly associated with the highest and lowest point of the blood pressure. In addition, with this analysis, the external pressure needed to achieve zero transmural pressure can be determined. When zero transmural pressure is achieved, the PPG waveform reflects the highest amplitude, as shown at area 814 in the PPG signal graph 802. In FIG. 8, as the amount of applied pressure follows the profile 808 of rapid increase and gradual decrease over time, the PPG waveform 806 changes in amplitude accordingly. Thus, looking at the entire range of PPG waveform from 810 to 812 with respect to applied force 808, the highest amplitude PPG waveform 814 provides an indication of the corresponding position on the applied pressure graph 804 where an amount of applied pressure results in zero transmural pressure state.

II. System Architecture

One exemplary embodiment of the optical measurement device is described in further detail below, including its components and their relationships. In the exemplary embodiment below, the feedback unit and corresponding interface, processing and display is described for an Apple® iPhone®, although one of skill in the art will recognize that other portable devices may be used.

A. Interaction Between Illumination/Detection Assembly and the Feedback Unit

The illumination and detection assembly 602 may be connected with the feedback unit 606, in this case a portable device such as an iPhone®, using the 30 pin connector at the base of the feedback unit 606. After establishing physical connection of the illumination and detection assembly 602 with the feedback unit 606 or any other form of processing device, a microcontroller unit (MCU) 640 (see FIG. 17) in the illumination and detection assembly 602 extracts information for authentication purposes prior to sending of data to the feedback unit 606 or any other form of processing device. This authentication process may be specific to the iPhone®, as Apple® requires that any device using the 30 pin connector purchase an authentication token from Apple®.

With the example of an iPhone®, communication is enabled via the Universal Asynchronous Receiver/Transmitter (UART) protocol from the 30 pin connector of the iPhone®. Strings of data are sent to UART every 8 milliseconds from the MCU of the illumination and detection assembly 602 to the iPhone®.

The data is comprised of 2 bytes of header and 10 bytes of payload. The payload is sub-divided into 5 parts, each comprising 2 bytes of data: DC1 (IR), DC2 (Red), PPG1 (IR), PPG2 (Red) and FS (Force Sensor). This data is obtained in a HEX file format and is then converted to back to voltage (V).

Figure 1:
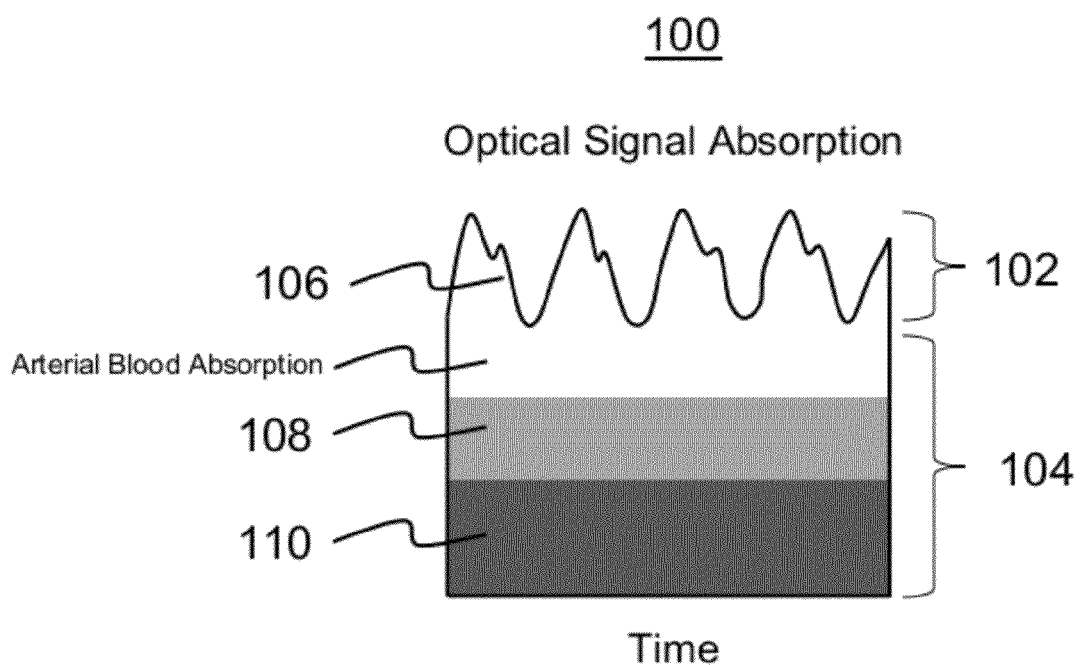
FIG. 1 is an illustration of a photoplethysmograph (PPG) and the components thereof, as is conventional in the art.
Figure 2:
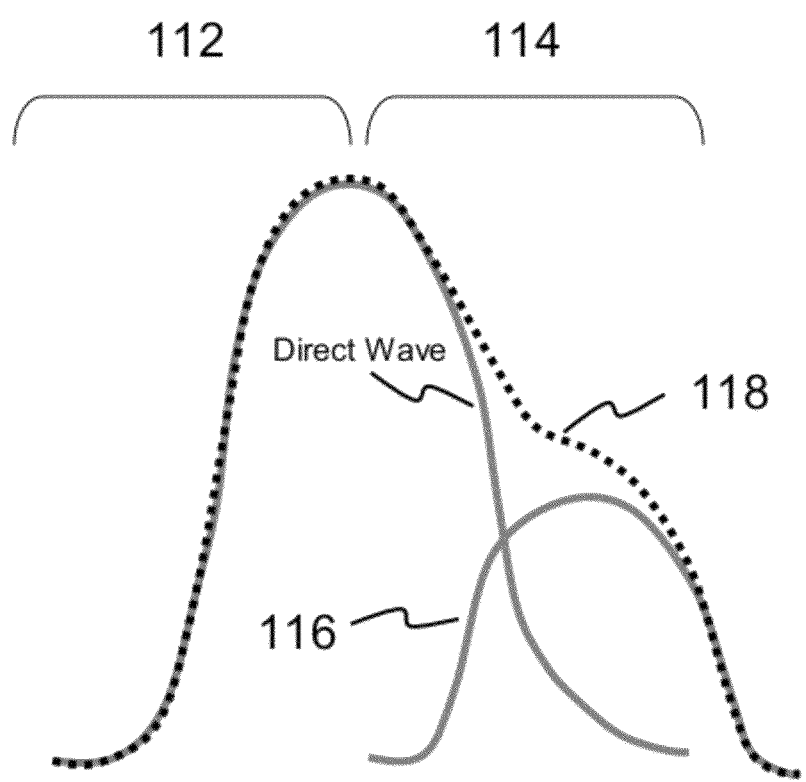
FIG. 2 is an illustration of an AC pulse waveform of the PPG, as is conventional in the art.

Referring back to FIG. 1, DC1 and DC2 provide information for the DC component 104 of the PPG waveform, thus enabling calculation for saturation of peripheral oxygen, or SpO$_2$. PPG1 and PPG2 establish the actual PPG waveform and provide information for the AC component 102 of the PPG waveform. FS sets out to provide information of the amount of pressure applied to the illumination and detection assembly 602. An example of the data decoding format is show in Table 1, below.

TABLE 1

Data Decoding Format

| Time (ms) | Data from Device | DC1 (Hex) | DC2 (Hex) | PPG1 (Hex) | PPG2 (Hex) | FS (Hex) | DC1 (V) | DC2 (V) | PPG1 (V) | PPG2 (V) | FS (V) |
|---|---|---|---|---|---|---|---|---|---|---|---|
| 0 | F0E20A01023A01F00350055E | 0701 | 023A | 01F0 | 0350 | 055E | 2.8905 | 0.9189 | 0.7996 | 1.3671 | 2.2150 |
| 8 | F0E20A01023A02A80347056D | 0701 | 023A | 02A8 | 0347 | 056D | 2.8905 | 0.9189 | 1.0962 | 1.3526 | 2.2392 |
| 16 | F0E20A01023A031802B7057A | 0701 | 023A | 0318 | 02B7 | 057A | 2.8905 | 0.9189 | 1.2768 | 1.1204 | 2.2602 |
| 24 | F0E20A01023A0314026D0584 | 0701 | 023A | 0314 | 026D | 0584 | 2.8905 | 0.9189 | 1.2703 | 1.0011 | 2.2763 |
| 32 | F0E20A01023A029E02D0058C | 0701 | 023A | 029E | 02D0 | 058C | 2.8905 | 0.9189 | 1.0801 | 1.1607 | 2.2892 |
| 40 | F0E20A01023A01E303550591 | 0701 | 023A | 01E3 | 0355 | 0591 | 2.8905 | 0.9189 | 0.7787 | 1.3751 | 2.2973 |
| 48 | F0E20A01023A012D03400592 | 0701 | 023A | 012D | 0340 | 0592 | 2.8905 | 0.9189 | 0.4852 | 1.3413 | 2.2989 |
| 56 | F0E20A01023A00C402AE0591 | 0701 | 023A | 00C4 | 02AE | 0591 | 2.8905 | 0.9189 | 0.3160 | 1.1059 | 2.2973 |
| 64 | F0E20A01023A00D0026E058D | 0701 | 023A | 00D0 | 026E | 058D | 2.8905 | 0.9189 | 0.3353 | 1.0027 | 2.2908 |
| 72 | F0E20A01023A014D02DB0585 | 0701 | 023A | 014D | 02DB | 0585 | 2.8905 | 0.9189 | 0.5368 | 1.1785 | 2.2779 |
| 80 | F0E20A01023A0209035A057B | 0701 | 023A | 0209 | 035A | 057B | 2.8905 | 0.9189 | 0.8399 | 1.3832 | 2.2618 |
| 88 | F0E20A01023A02BC0338056E | 0701 | 023A | 02BC | 0338 | 056E | 2.8905 | 0.9189 | 1.1285 | 1.3284 | 2.2408 |
| 96 | F0E20A01023A031F02A5055F | 0701 | 023A | 031F | 02A5 | 055F | 2.8905 | 0.9189 | 1.2881 | 1.0914 | 2.2167 |
| 104 | F0E20A01023A030B0270054E | 0701 | 023A | 030B | 0270 | 054E | 2.8905 | 0.9189 | 1.2558 | 1.0060 | 2.1893 |
| 112 | F0E20A01023A028802E5053B | 0701 | 023A | 0288 | 02E5 | 053B | 2.8905 | 0.9189 | 1.0447 | 1.1946 | 2.1586 |
| 120 | F0E20A01023A01F00350055E | 0701 | 023A | 01C9 | 035E | 0526 | 2.8905 | 0.9189 | 0.7367 | 1.3896 | 2.1240 |

B. Signal Conditioning

A raw PPG signal includes DC and AC components, both of which containing information critical for waveform analysis. Signal conditioning is therefore performed in order to obtain the information for further processing at the feedback unit. One embodiment of the signal conditioning process will be described below, and may be carried out by components of the illumination and detection assembly 602 illustrated in the block diagram of FIG. 17.

To determine the DC component of the PPG signal, the raw signal 642 obtained from a photodetector 610 is digitized at ADC1 644. The digitized signal will be passed on to both buffer (IR) 646 and buffer (Red) 648 accordingly, which will store up to 100 samples each before sending collated data to the processor 650.

Using the raw samples, a baseline DC component can be determined by the processor 650. At the processor 650, the digital values for Vsub (IR) and Vsub (RED) (i.e. the DC components) are calculated. The Vsub signals 652 are subsequently converted by a digital-to-analog converter (DAC) 654.

The determined DC component (Vsub) is then subtracted from the raw signal, Vraw to obtain Vac 656. The new raw signal, Vac 656, then undergoes a second stage amplification at a second stage amplifier 658 to obtain Vppg 660, where the signal to noise ratio is improved compared with Vraw 642.

Figure 18A:
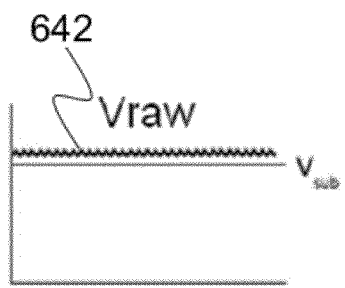
FIGS. 18A, 18B and 18C are graphical illustrations of signals used in the process of obtaining a direct current (DC) component of the PPG signal, according to an exemplary embodiment.
Figure 18B:
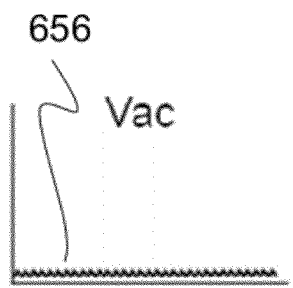
Figure 18C:
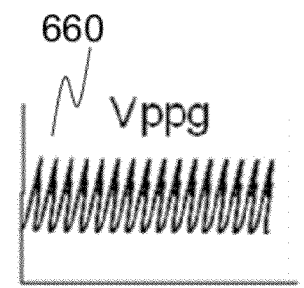
Figure 19:
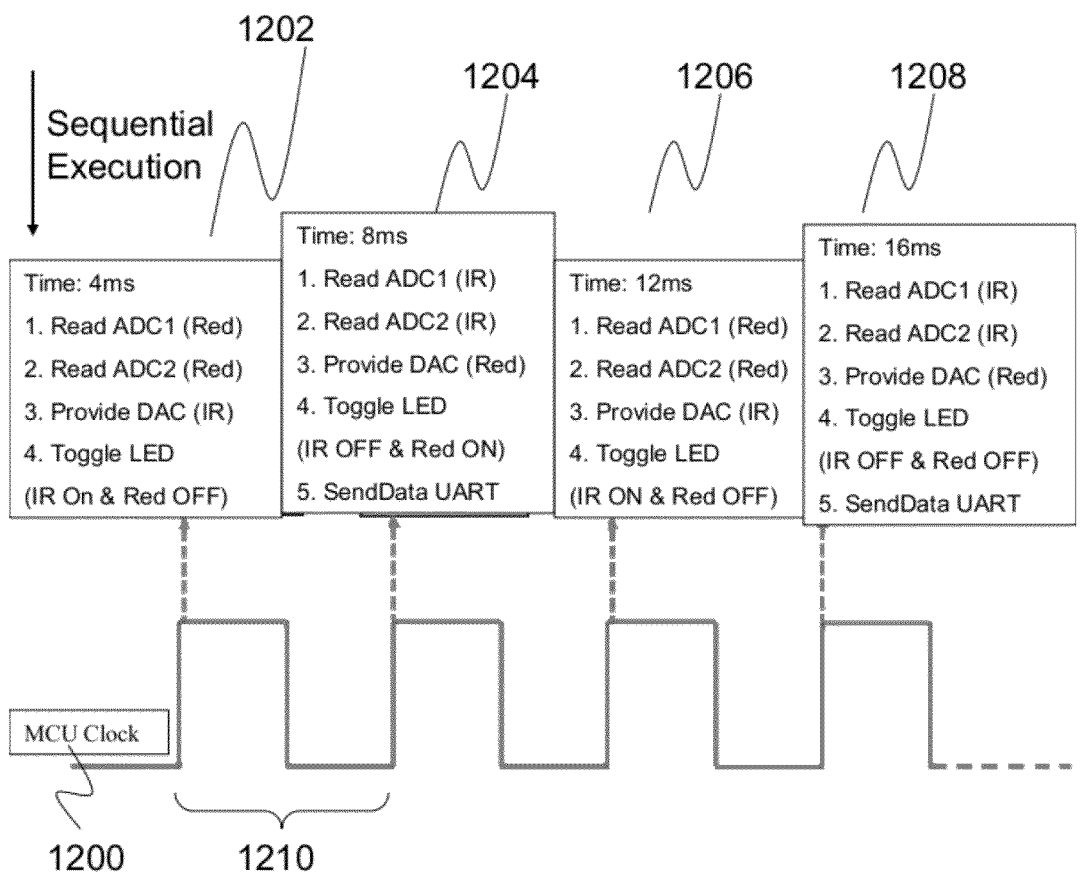
FIG. 19 is an illustration of a sequence of data collection performed during the process of obtaining the PPG signal, according to an exemplary embodiment.

The resolution of the new raw signal 660 is thus enhanced substantially when digitized at ADC2 662, as can be seen from the graphical representations of the Vraw signal 642 in FIG. 18A, Vac 656 in FIG. 18B, and Vppg 660 in FIG. 18C.

Referring to FIG. 12, in order to collect the data, an MCU clock 1200 is set to toggle at a predetermined interval to accommodate retrieving results from both LED (IR) 664 and LED (RED) 666 during a respective first interval 1202 and second interval 1204. In the non-limiting embodiment shown in FIG. 12, the interval 1210 is set to 4 milliseconds. The data collection sequence is then repeated in the third interval 1206 and fourth interval 1208. Before each toggle between the two LEDs, data from ADC1 644 and ADC2 662 are taken and sent to UART.

III. Method of Operation

Figure 20:
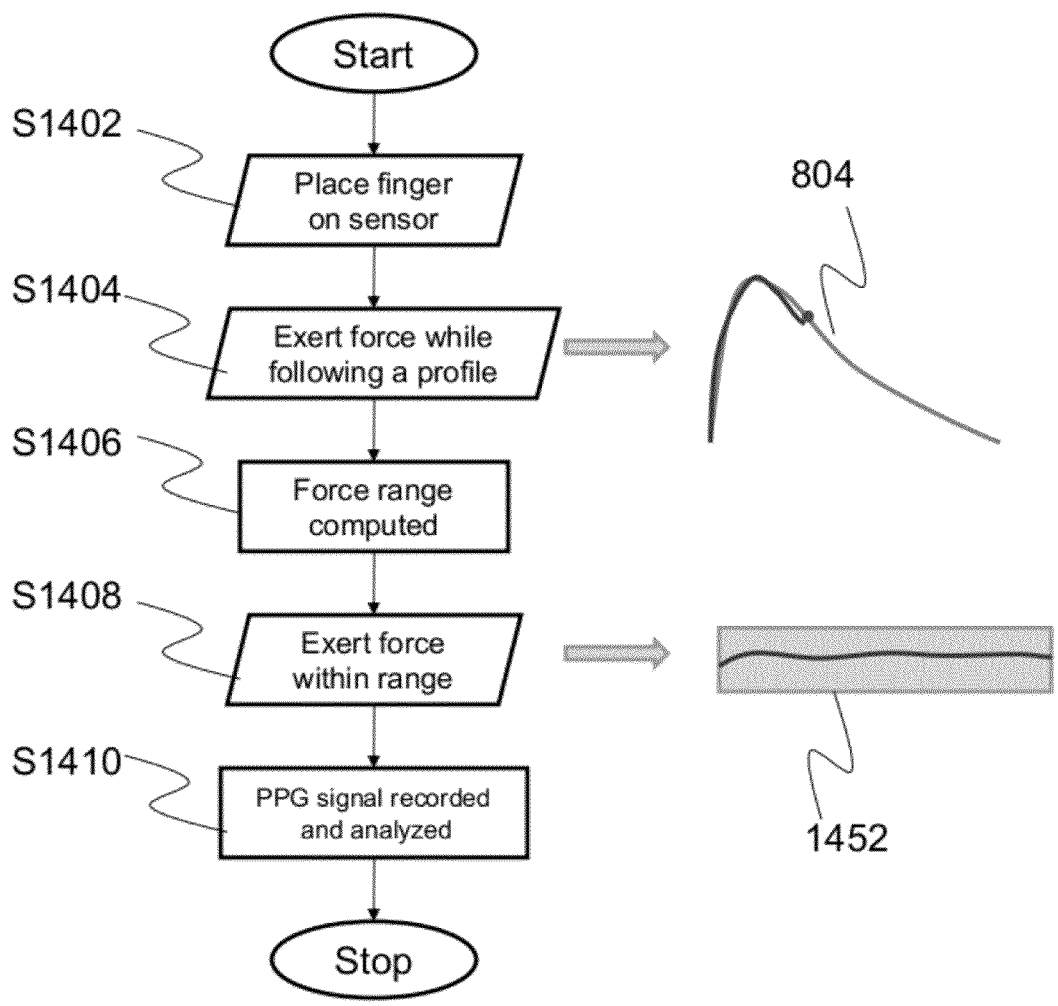
FIG. 20 is a flow chart illustrating a method of measuring the PPG signal on the optical measurement device using feedback from the pressure detection assembly, according to an exemplary embodiment.
Figure 21:
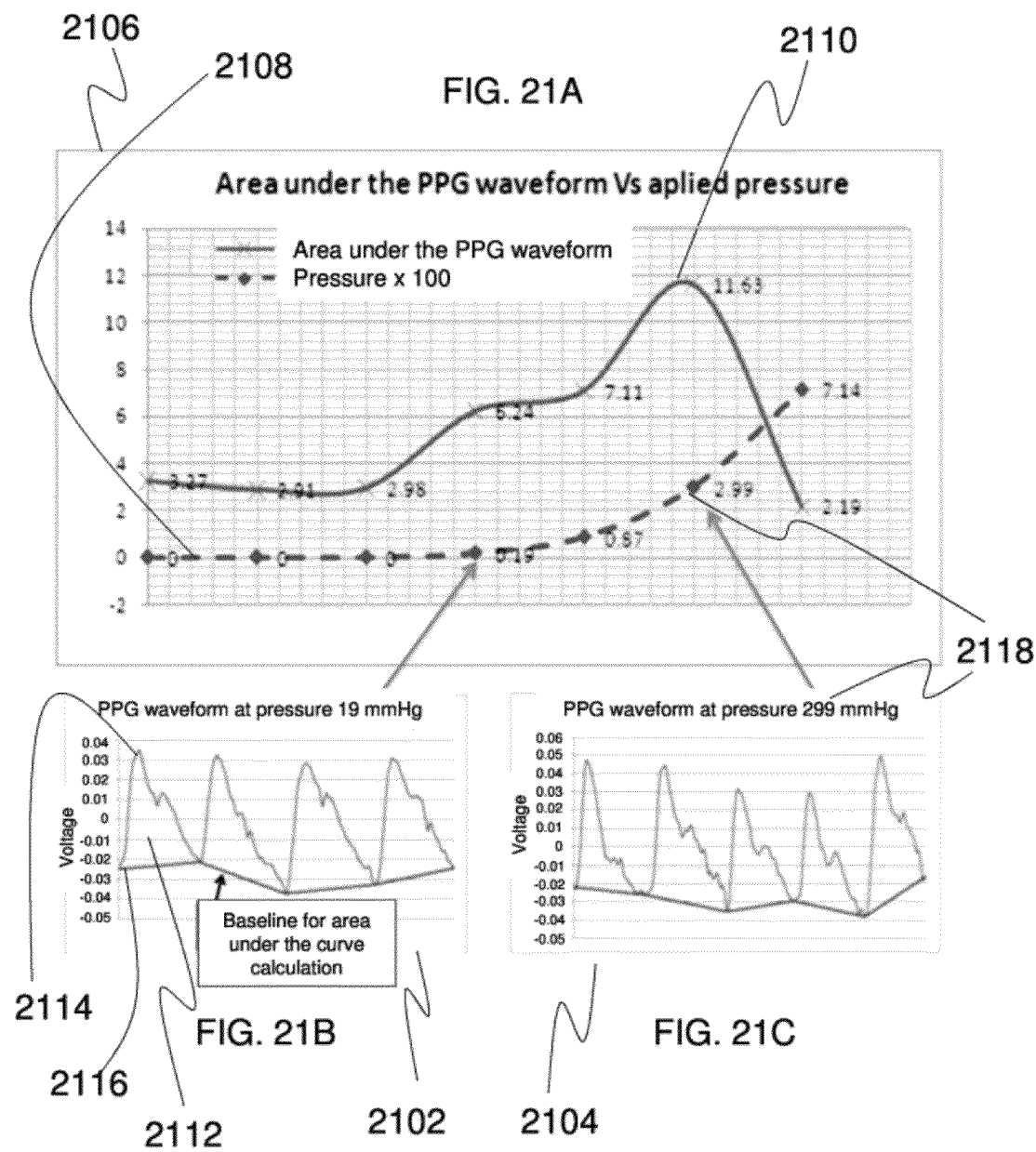
FIGS. 21A, 21B and 21C are graphical representations of the correlation between a PPG waveform and an applied pressure, as would be used in the method of measuring an optimal PPG signal, according to an exemplary embodiment.

One exemplary embodiment of a method of using the optical measurement device is described herein with reference to FIG. 20, with a corresponding exemplary GUI illustrated in FIGS. 21A-21C. A user seeking to obtain his or her PPG signals will first place a body part, such as a finger, on the sensor surface of the optical measurement device (S1402). Calibration of the device to the individual user may be performed (S1404), where the user is asked to apply an amount of pressure over a specific period of time, corresponding to a force profile 804, (see FIG. 8). In other words, the user is asked to vary the applied pressure such that the system can determine an optimum pressure for the user by analyzing the resulting PPG waveforms that result from the variety of applied pressures (S1406). The user may also be presented with at least one measured PPG waveform generated by a particular amount of applied pressure, as illustrated in the graphical displays in FIGS. 21B and 21C. FIG. 21A is a graphical display 2106 which shows the relationship of a calculated area 2110 under the curve in FIGS. 21B and 21C with respect to applied pressure 2108. FIGS. 21B and 21C are graphical displays 2102 and 2104, respectively, which illustrate the different PPG waveforms at different applied pressures, and how the area under curve of the PPG waveform is computed. As shown in FIG. 21A, the optimum pressure 2118 applied in FIG. 21C, 299 mmHg, corresponds to the largest area 2110 of PPG waveform detected during the calibration (S1404). Once this optimum pressure is determined, a subsequent measurement period begins, during which the user is asked to apply pressure within an optimum range above and below the optimum pressure (S1408). As previously described with regard to FIG. 9A, the amount of pressure being applied by the user may be displayed in a graph 618 on the display 614 so that the user can see the amount of pressure being applied in real-time. The graph 618 may also be displayed using the pressure status bar 620. If the amount of force being applied by the user falls outside of the optimum range, the system can detect this in real-time and will ask the user to increase or decrease the applied pressure in order to remain within the range of optimum pressure and record the best possible PPG signal quality (S1410).

Optimum pressure is determined as the pressure at which the measured PPG signal has the largest waveform amplitude, or area 2112 under the PPG waveform, as shown in FIG. 21B by the area 2112 bounded by the PPG signal 2114 and baseline 2116. FIG. 21A then graphs the variation of the area 2112 under the PPG waveform with respect to the pressure 2108 applied on the sensor. As may be observed in this example, the optimum pressure 2118 is at 299 mmHg, where area 2112 under the curve is at its maximum of 11.63.

Figure 22:
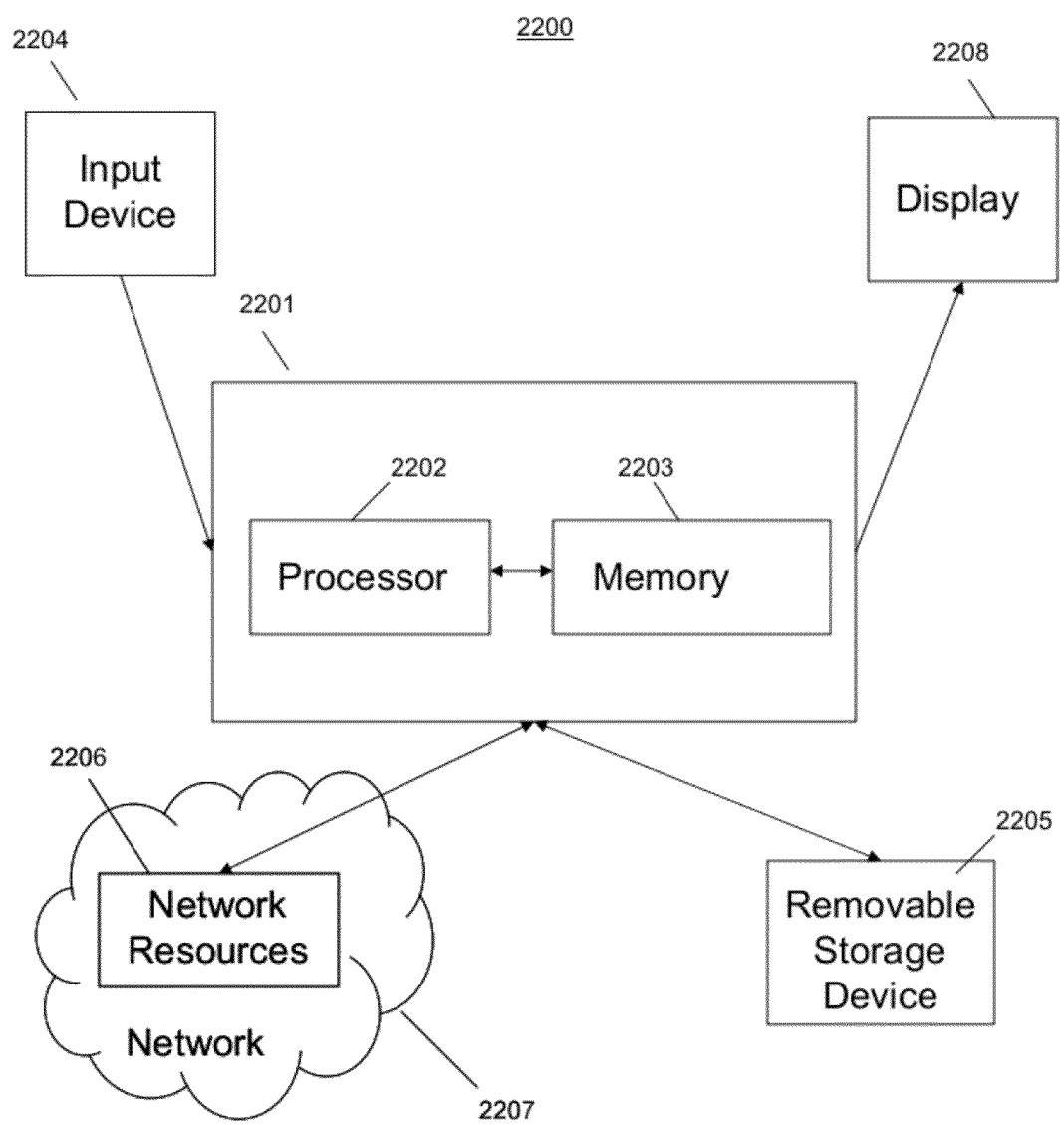
FIG. 22 is a block diagram of a computer system upon which the device and methods may be implemented, according to an exemplary embodiment.

FIG. 22 is a block diagram that illustrates an embodiment of a computer/server system 2200 upon which an embodiment of the inventive methodology may be implemented. The system 2200 includes a computer/server platform 2201 including a processor 2202 and memory 2203 which operate to execute instructions, as known to one of skill in the art. The term "computer-readable medium" as used herein refers to any medium that participates in providing instructions to processor 2202 for execution. Additionally, the computer platform 2201 receives input from a plurality of input devices 2204, such as a keyboard, mouse, touch device or verbal command. The computer platform 2201 may additionally be connected to a removable storage device 2205, such as a portable hard drive, optical media (CD or DVD), disk media or any other medium from which a computer can read executable code. The computer platform may further be connected to network resources 2206 which connect to the Internet or other components of a local public or private network. The network resources 2206 may provide instructions and data to the computer platform from a remote location on a network 2207. The connections to the network resources 2206 may be via wireless protocols, such as the 802.11 standards, Bluetooth® or cellular protocols, or via physical transmission media, such as cables or fiber optics. The network resources may include storage devices for storing data and executable instructions at a location separate from the computer platform 2201. The computer interacts with a display 2208 to output data and other information to a user, as well as to request additional instructions and input from the user. The display 2208 may therefore further act as an input device 2204 for interacting with a user.

What is claimed is:

1. An optical measurement device comprising:
  an illumination and detection assembly configured to output light to a portion of living tissue of a user and detect transmitted or reflected light as a signal; and
  a pressure assembly configured to detect an amount of pressure applied to the illumination and detection assembly by the portion of living tissue of the user,
  wherein the illumination and detection assembly and the pressure assembly are capable of communicating with a feedback unit configured to correlate a quality of the detected signal with the amount of applied pressure by:
    computing an area under waveforms of detected signals corresponding to a variety of applied pressure amounts, and
    determining an optimum pressure to correspond a largest computed area, from the variety of applied pressure amounts,
  wherein the feedback unit is further configured to provide a feedback related to the optimum pressure to the user.

2. The optical measurement device of claim 1, wherein the feedback is an indication of whether the user should adjust the amount of pressure being applied to the illumination and detection assembly.

3. The optical measurement device of claim 2, wherein the feedback is displayed as a range of optimal applied pressures along with the actual applied pressure being applied by the user.

4. The optical measurement device of claim 3, wherein the range of optimal applied pressures corresponds to a state of zero transmural pressure.

5. The optical measurement device of claim 2, wherein the feedback is a request to the user to increase, decrease or maintain the applied pressure.

6. The optical measurement device of claim 1, wherein the feedback is a real-time visual output of the detected signal and detected applied pressure.

7. The optical measurement device of claim 1, wherein the feedback unit is a portable computer including a processor, memory and a display.

8. The optical measurement device of claim 7, wherein the illumination and detection assembly, pressure assembly and feedback unit are integrated into a portable device.

9. The optical measurement device of claim 8, wherein the portable device is configured with a plurality of illumination and detection assemblies and a plurality of pressure assemblies.

10. The optical measurement device as claimed in claim 7, wherein the portable computer comprises one of a mobile phone, a smartphone, a personal digital assistant (PDA), a tablet, a netbook and a laptop.

11. The optical measurement device of claim 1, wherein the illumination and detection assembly and the pressure assembly are capable of communicating with the feedback unit over a wireless network.

12. The optical measurement device of claim 1, wherein the detected signal is a photoplethysmography (PPG) signal.

13. The optical measurement device of claim 1, wherein the illumination and detection assembly and pressure assembly are integrated into a single portable device.

14. The optical measurement device of claim 13, wherein the feedback unit is provided separately and is configured to be connectable to the optical measurement device.

15. The optical measurement device of claim 1, wherein the pressure assembly comprises a thin film flexible printed circuit.

16. The optical measurement device of claim 1, wherein the illumination and detection assembly comprises a red light emitting diode (LED), an infra-red LED or both.

17. The optical measurement device of claim 16, wherein saturation of peripheral oxygen ($SPO_2$) information of the user is derivable from the detected light information from both the red LED and the infra-red LED.

18. A method for detecting a physiological signal using an optical measurement device, the method comprising:
   illuminating a portion of living tissue of a user and detecting transmitted or reflected light as a signal using an illumination and detection assembly;
   detecting an amount of pressure applied by the portion of living tissue of the user to the illumination and detection assembly using a pressure detection assembly; and
   correlating a quality of the detected signal with the amount of applied pressure:
      computing an area under waveforms of detected signals corresponding to a variety of applied pressure amounts, and
      determining an optimum pressure to correspond a largest computed area, from the variety of applied pressure amounts.

19. The method of claim 18, further comprising providing feedback related to the optimum pressure to the user using a feedback unit.

20. The method of claim 19, wherein the step of providing feedback comprises providing an indication to the user of whether the amount of pressure being applied to the illumination and detection assembly should be adjusted.

21. The method of claim 20, wherein the step of providing feedback further comprises displaying a range of optimal applied pressures along with the actual applied pressure being applied by the user.

22. The method of claim 21, wherein the step of providing feedback further comprises displaying a range of optimal applied pressures which corresponds to a state of zero transmural pressure.

23. The method of claim 20, wherein the step of providing feedback further comprises requesting the user to increase, decrease or maintain the applied pressure.

24. The method of claim 19, wherein the step of providing feedback further comprises displaying a real-time visual output of the detected signal and the detected applied pressure.

25. The method of claim 19, wherein the feedback unit is a portable computer including a processor, memory and a display.

26. The method of claim 25, wherein the illumination and detection assembly, pressure assembly and feedback unit are integrated into a portable device.

27. The method of claim 26, wherein the portable device is configured with a plurality of illumination and detection assemblies and a plurality of pressure assemblies.

28. The method of claim 25, wherein the portable computer is one selected from the group consisting of a mobile phone, a smartphone, a personal digital assistant (PDA), a tablet, a netbook and a laptop.

29. The method of claim 19, wherein the step of providing feedback comprises wirelessly communicating between the feedback unit and the illumination and detection assembly and pressure assembly.

30. The method of claim 18, wherein the detected signal is a photoplethysmography (PPG) signal.

31. The method of claim 19, wherein the illumination and detection assembly and pressure assembly are integrated into a single portable device.

32. The method of claim 31, wherein the feedback unit is provided separately and is configured to be connectable to the optical measurement device.

33. The method of claim 18, wherein the pressure assembly comprises a thin film flexible printed circuit.

34. The method of claim 18, wherein the illumination and detection assembly comprises a red light emitting diode (LED), an infra-red LED or both.

35. The method of claim 34, further comprising deriving saturation of peripheral oxygen ($SPO_2$) information of the user from the detected output light information from both the red LED and the infra-red LED.

36. A computer program product for detecting a physiological signal using an optical measurement device, the computer program product embodied on a computer readable medium and when executed by a computer with a processor and a memory, performs the method comprising:
   illuminating a portion of living tissue of a user and detecting transmitted or reflected light as a signal using an illumination and detection assembly;
   detecting an amount of pressure applied by the portion of living tissue of the user to the illumination and detection assembly; and
   correlating a quality of the detected signal with the amount of applied pressure:
      computing an area under waveforms of detected signals corresponding to a variety of applied pressure amounts, and
      determining an optimum pressure to correspond a largest computed area, from the variety of applied pressure amounts.

37. The computer program product of claim 36, wherein the method further comprises providing feedback related to the optimum pressure to the user.

38. An optical measurement system comprising:
   an optical measurement device comprising:
      an illumination and detection assembly configured to output light to a portion of living tissue of a user and detect transmitted or reflected light as a signal; and
      a pressure assembly configured to detect an amount of pressure applied to the illumination and detection assembly by the portion of living tissue of the user; and a feedback unit connected to the optical measurement device, and configured to correlate a quality of the detected signal with the amount of applied pressure by:
   computing an area under waveforms of detected signals corresponding to a variety of applied pressure amounts, and
   determining an optimum pressure to correspond a largest computed area, from the variety of applied pressure amounts,
wherein the feedback unit is further configured to provide a feedback related to the optimum pressure to the user.

* * * * *